US 12,239,476 B2

United States Patent
Miyano et al.

(10) Patent No.: US 12,239,476 B2
(45) Date of Patent: Mar. 4, 2025

(54) BIOMETRIC INFORMATION DISPLAY APPARATUS, METHOD, AND PROGRAM

(71) Applicants: Yuki Miyano, Tokyo (JP); Taishi Watanabe, Tokyo (JP); Shigenori Kawabata, Tokyo (JP)

(72) Inventors: Yuki Miyano, Tokyo (JP); Taishi Watanabe, Tokyo (JP); Shigenori Kawabata, Tokyo (JP)

(73) Assignee: INSTITUTE OF SCIENCE TOKYO, Tokyo (JP)

( * ) Notice: Subject to any disclaimer, the term of this patent is extended or adjusted under 35 U.S.C. 154(b) by 351 days.

(21) Appl. No.: 17/756,276

(22) PCT Filed: Nov. 25, 2020

(86) PCT No.: PCT/JP2020/043875
§ 371 (c)(1),
(2) Date: May 20, 2022

(87) PCT Pub. No.: WO2021/106948
PCT Pub. Date: Jun. 3, 2021

(65) Prior Publication Data
US 2022/0409156 A1    Dec. 29, 2022

(30) Foreign Application Priority Data
Nov. 26, 2019  (JP) .................. 2019-213566
Apr. 17, 2020   (JP) .................. 2020-074272

(51) Int. Cl.
*A61B 6/46*   (2024.01)
*A61B 5/242*  (2021.01)
*A61B 5/248*  (2021.01)

(52) U.S. Cl.
CPC .............. *A61B 6/463* (2013.01); *A61B 5/242* (2021.01); *A61B 5/248* (2021.01)

(58) Field of Classification Search
CPC ......... A61B 6/463; A61B 5/242; A61B 5/248; A61B 5/246; A61B 6/5229; A61B 5/243
See application file for complete search history.

(56) References Cited

U.S. PATENT DOCUMENTS

2003/0097056 A1*  5/2003  Suzuki ............... A61B 5/243
                                                                600/409
2008/0009758 A1   1/2008  Voth
(Continued)

FOREIGN PATENT DOCUMENTS

JP    H11-104093    4/1999
JP    2003-144406   5/2003
(Continued)

OTHER PUBLICATIONS

International Search Report issued on Mar. 16, 2021 in PCT/JP2020/043875.

Primary Examiner — Zhitong Chen
(74) Attorney, Agent, or Firm — IPUSA, PLLC

(57) ABSTRACT

A biometric information display apparatus (30) for displaying a measurement result obtained by measuring a biometric signal, includes a maximum value calculation unit (63) configured to calculate a maximum value of the measurement result in a certain period of time for at least one of blocks into which a measurement area, in which the biometric signal is measured, is divided, a determination unit (64) configured to determine whether a measurement value in the at least one of blocks is greater than or equal to a threshold value obtained by multiplying the maximum value by a fractional value, the fractional value being determined in advance, and a display control unit configured to display, in response to an occurrence of an event in which the measurement value is determined to be greater than or equal (Continued)

to the threshold value, the measurement result in such a manner as to indicate the occurrence of the event.

13 Claims, 13 Drawing Sheets

(56) References Cited

U.S. PATENT DOCUMENTS

| | | |
|---|---|---|
| 2008/0033312 A1* | 2/2008 | Nakai .................... A61B 5/243 600/509 |
| 2013/0253349 A1 | 9/2013 | Hayam et al. |
| 2015/0208942 A1 | 7/2015 | Bar-Tal et al. |
| 2015/0366476 A1 | 12/2015 | Laughner et al. |
| 2016/0038047 A1 | 2/2016 | Urman et al. |
| 2017/0178403 A1 | 6/2017 | Krummen et al. |
| 2018/0333062 A1 | 11/2018 | Watanabe |
| 2019/0167135 A1 | 6/2019 | Okada et al. |

FOREIGN PATENT DOCUMENTS

| | | |
|---|---|---|
| JP | 5135333 | 2/2013 |
| JP | 2016-036731 | 3/2016 |
| JP | 6189060 | 8/2017 |
| JP | 6345806 | 6/2018 |
| JP | 2018-192236 | 12/2018 |
| JP | 2019-509070 | 4/2019 |
| JP | 2019-098156 | 6/2019 |
| JP | 6552828 | 7/2019 |

* cited by examiner

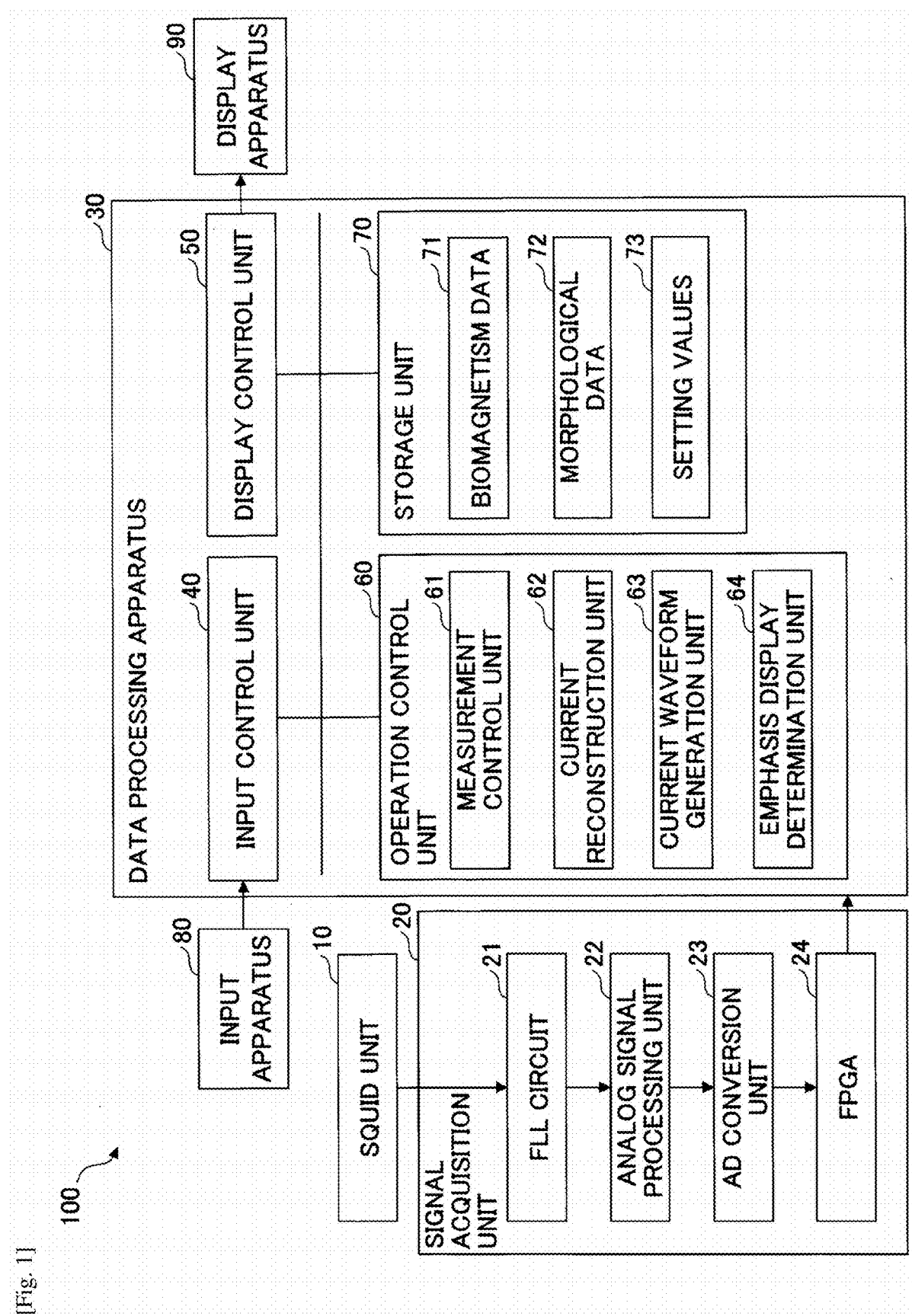
[Fig. 1]

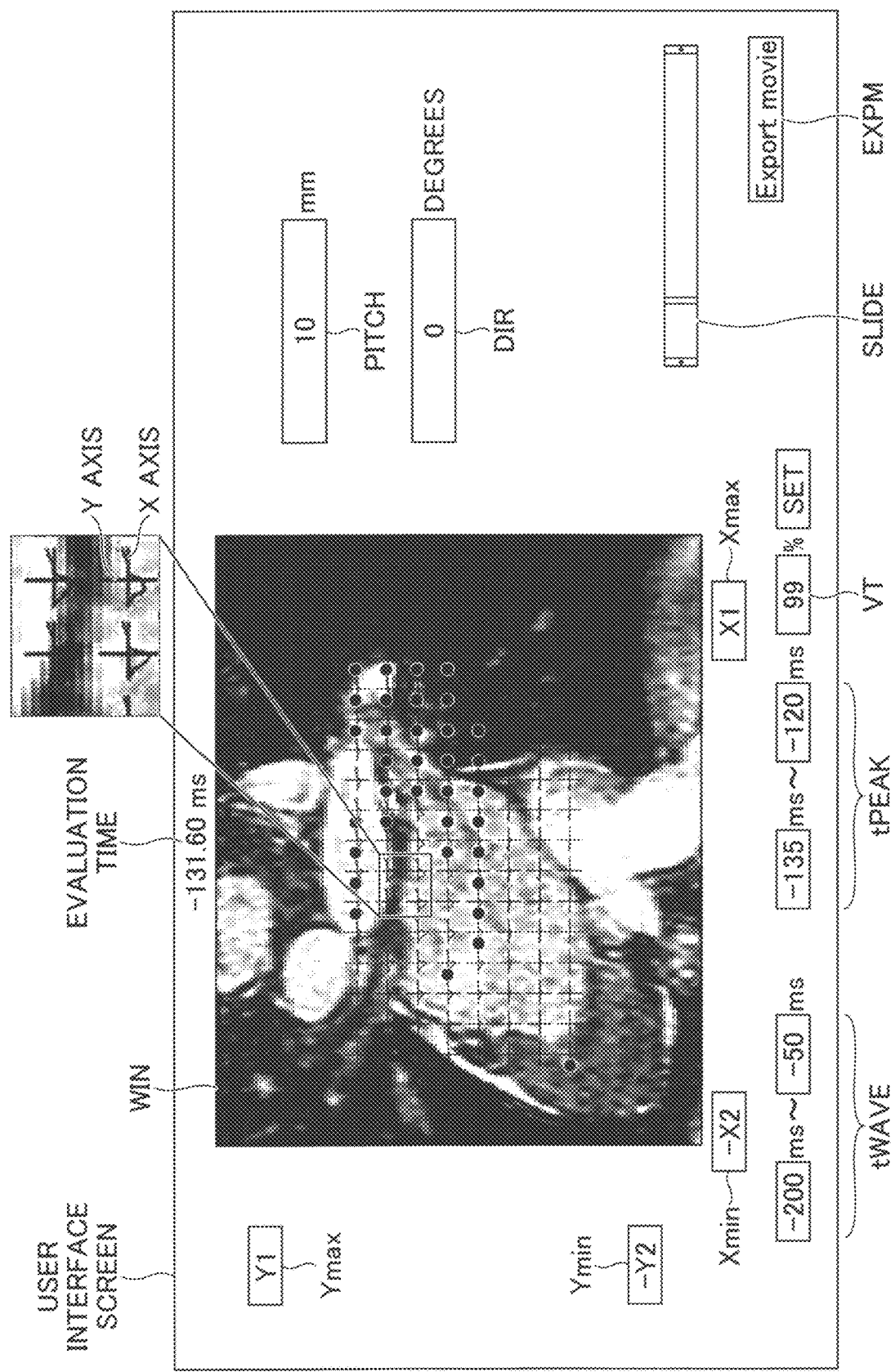
[Fig. 2]

[Fig. 3]
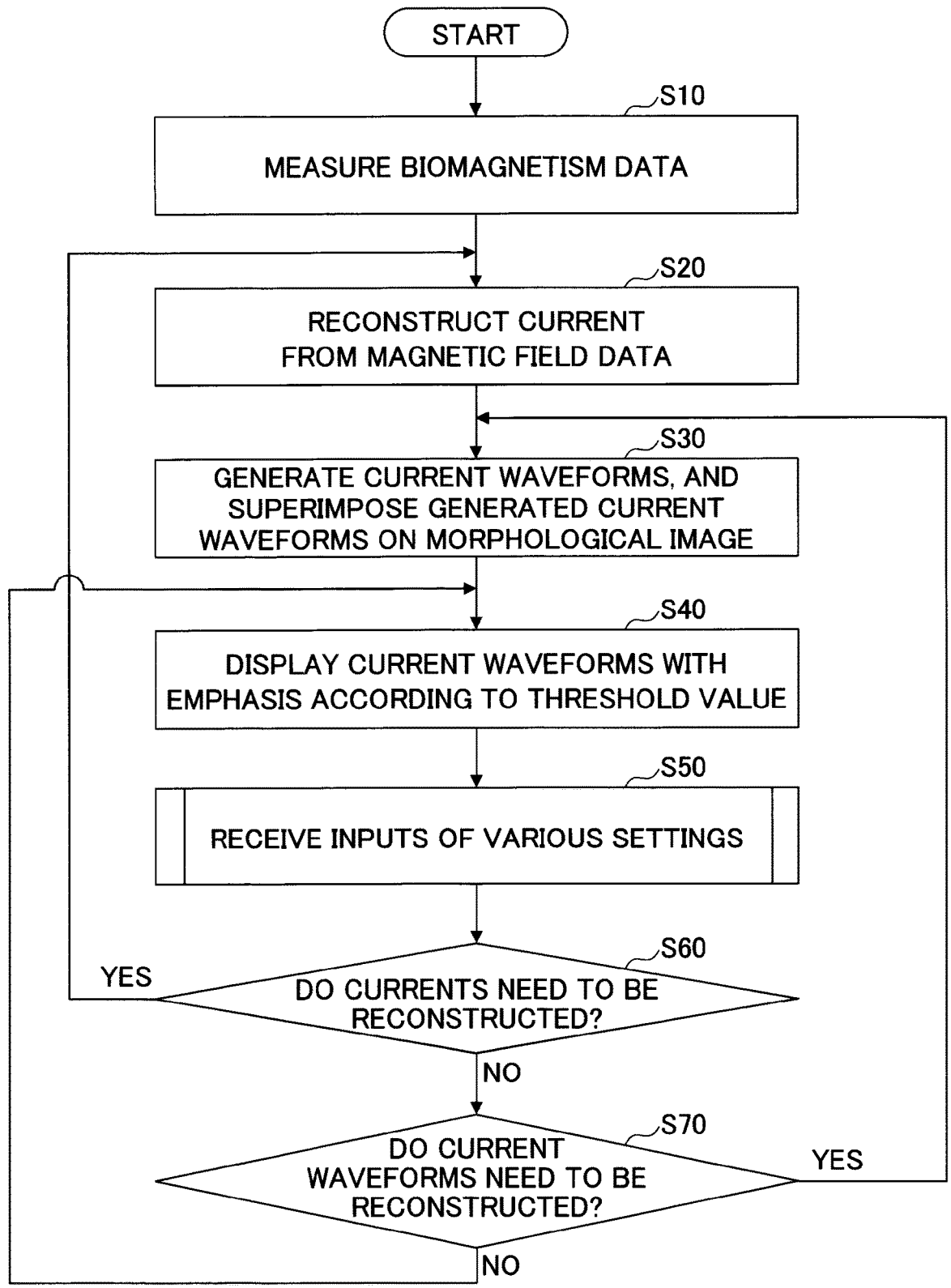

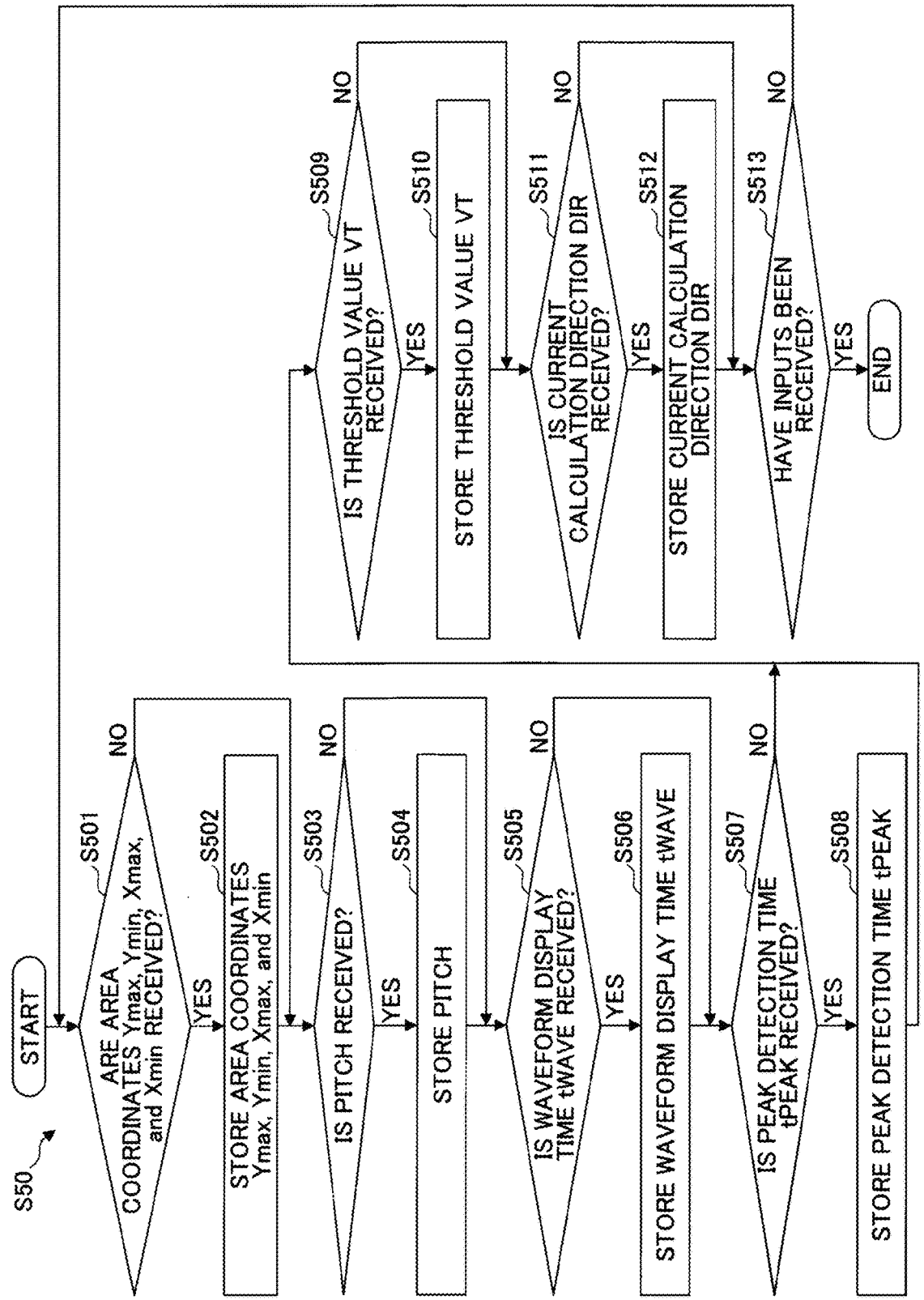
[Fig. 4]

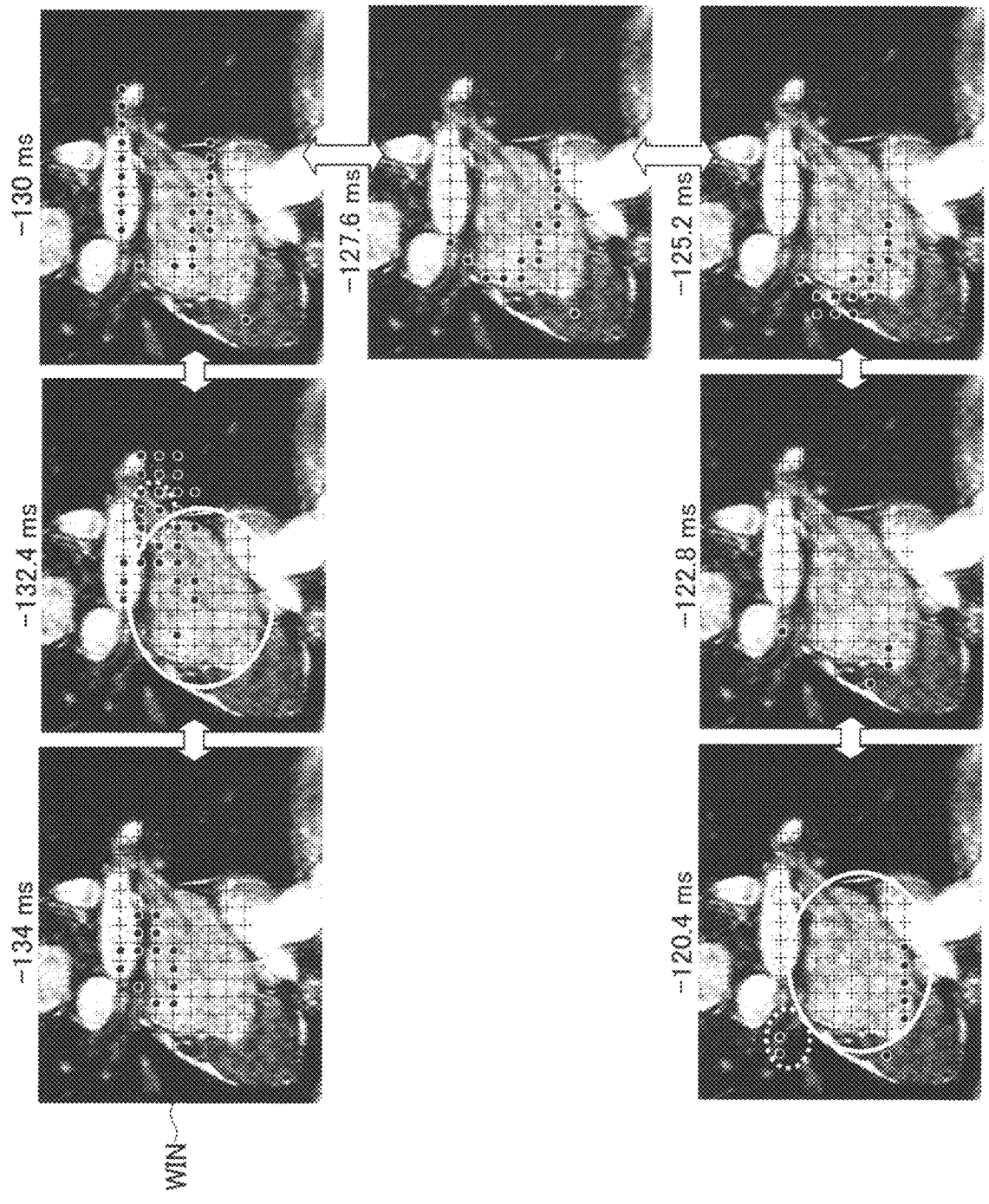
[Fig. 5]

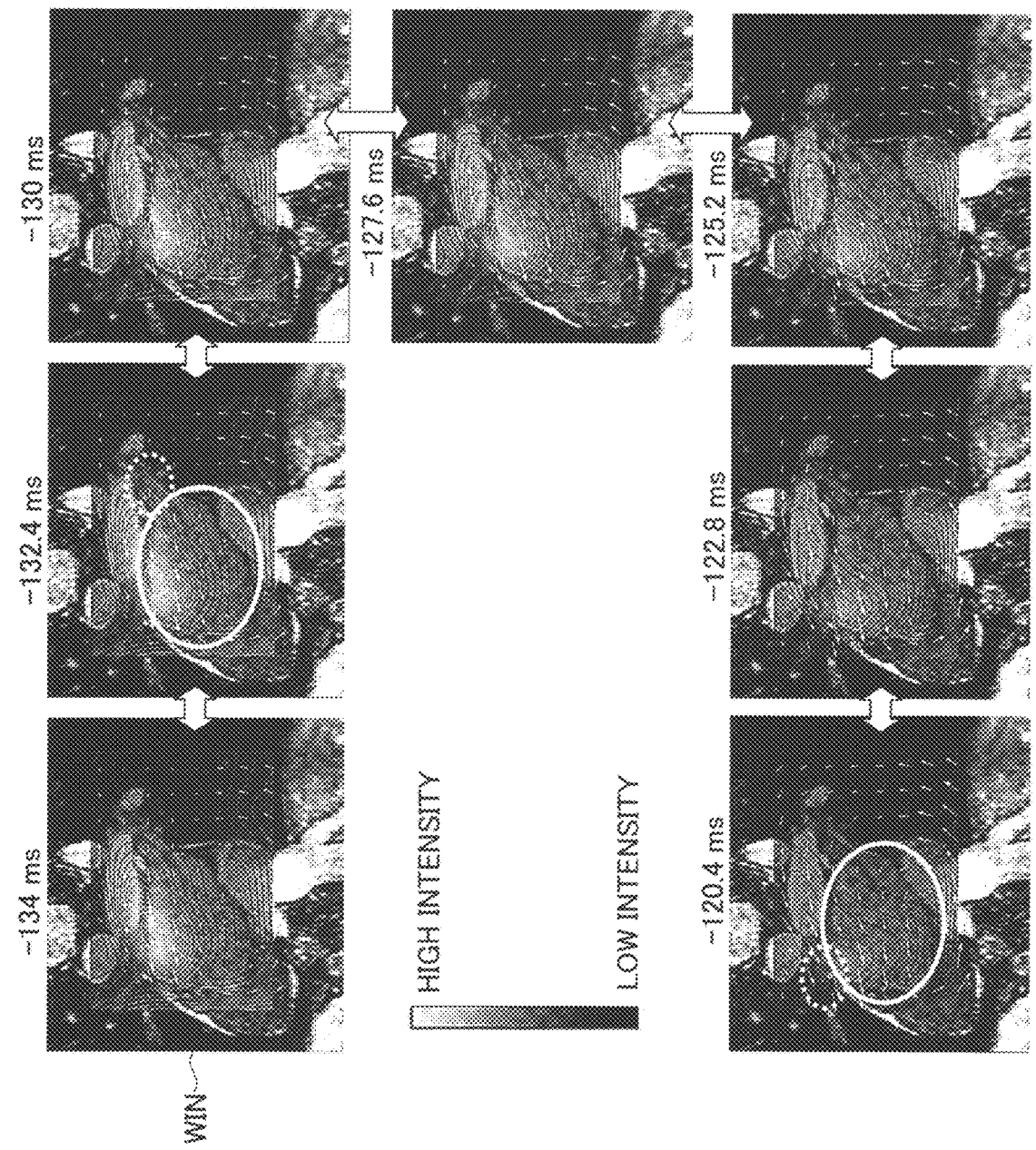
[Fig. 6]

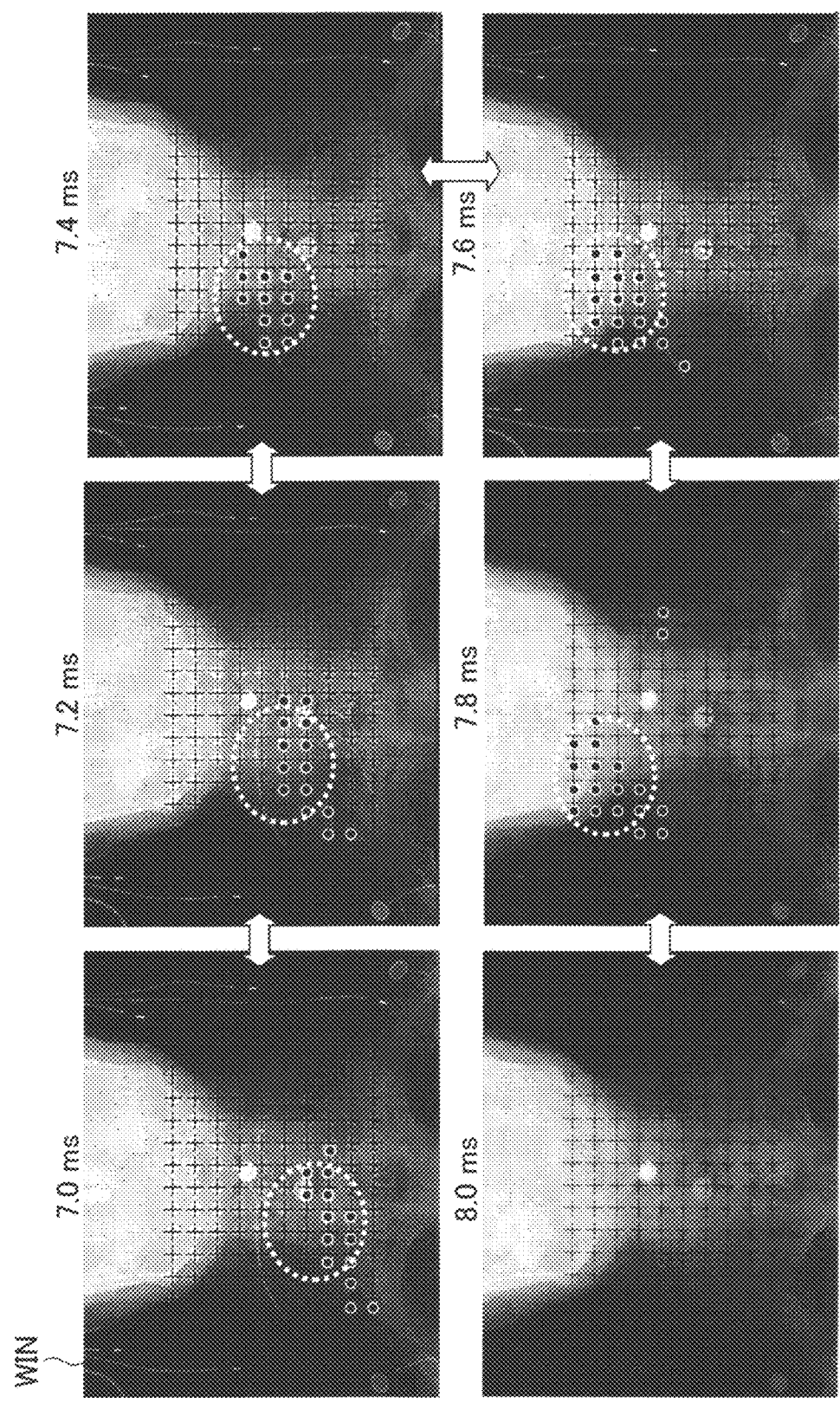

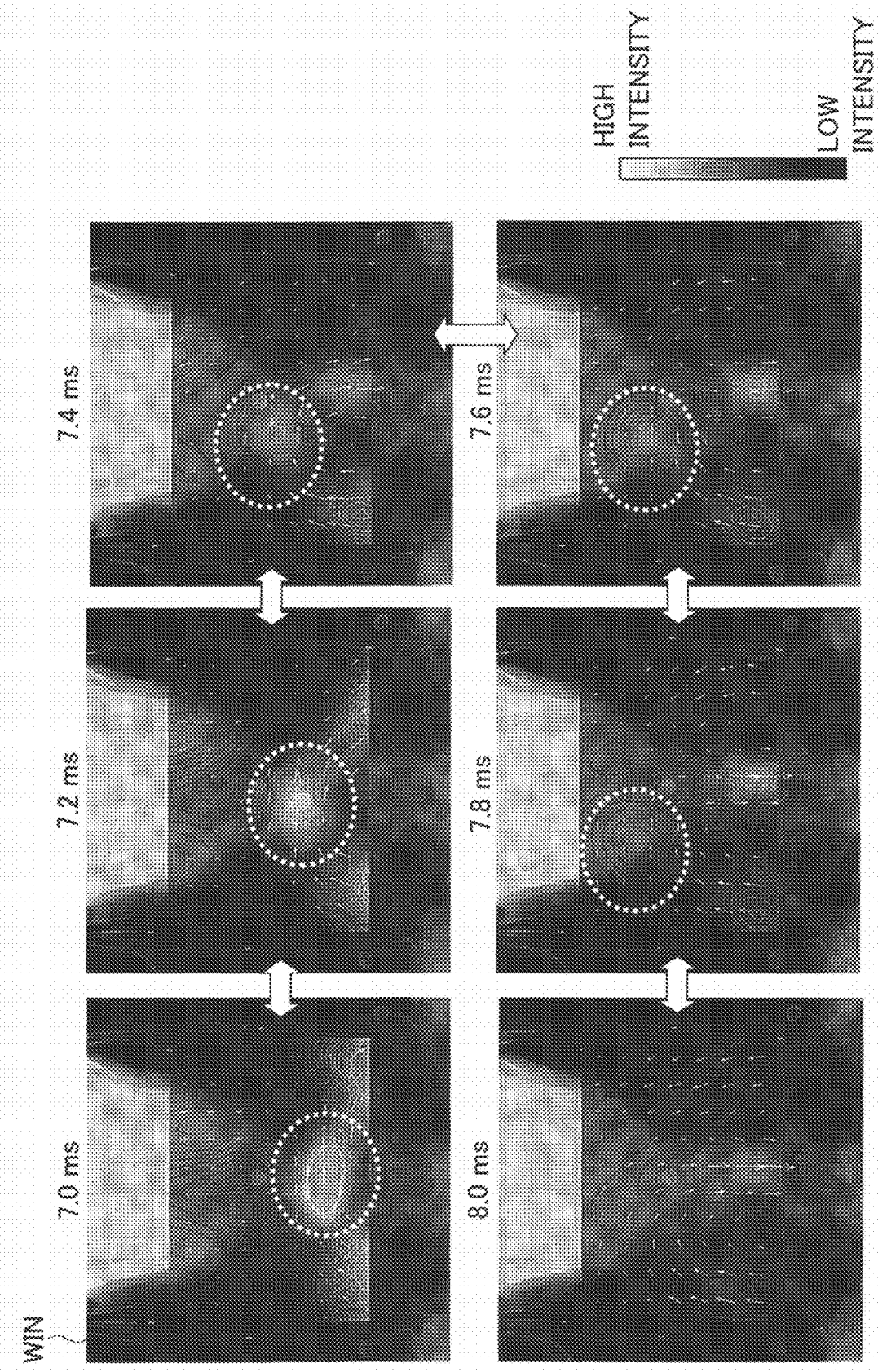
[Fig. 8]

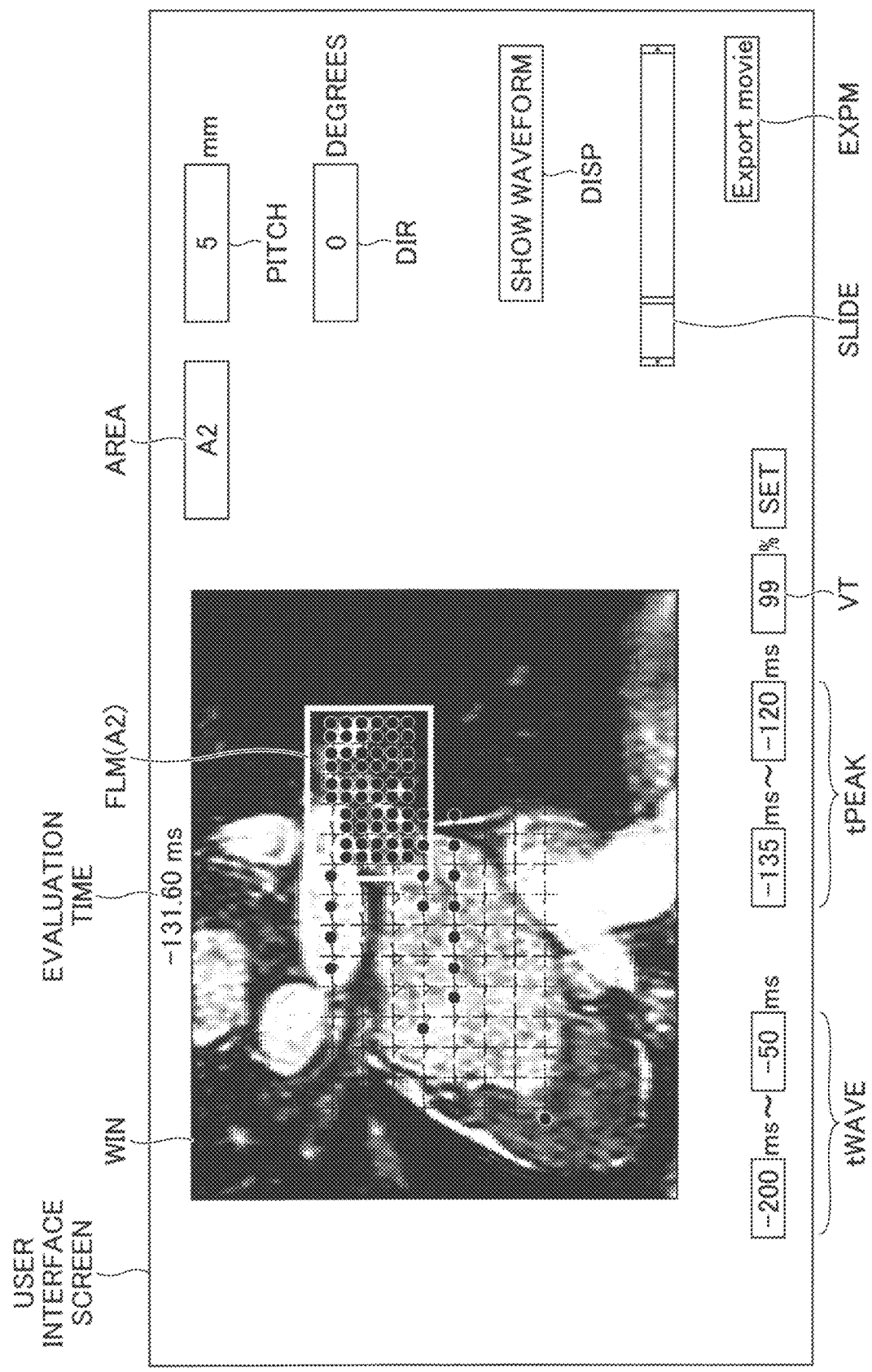
[Fig. 9]

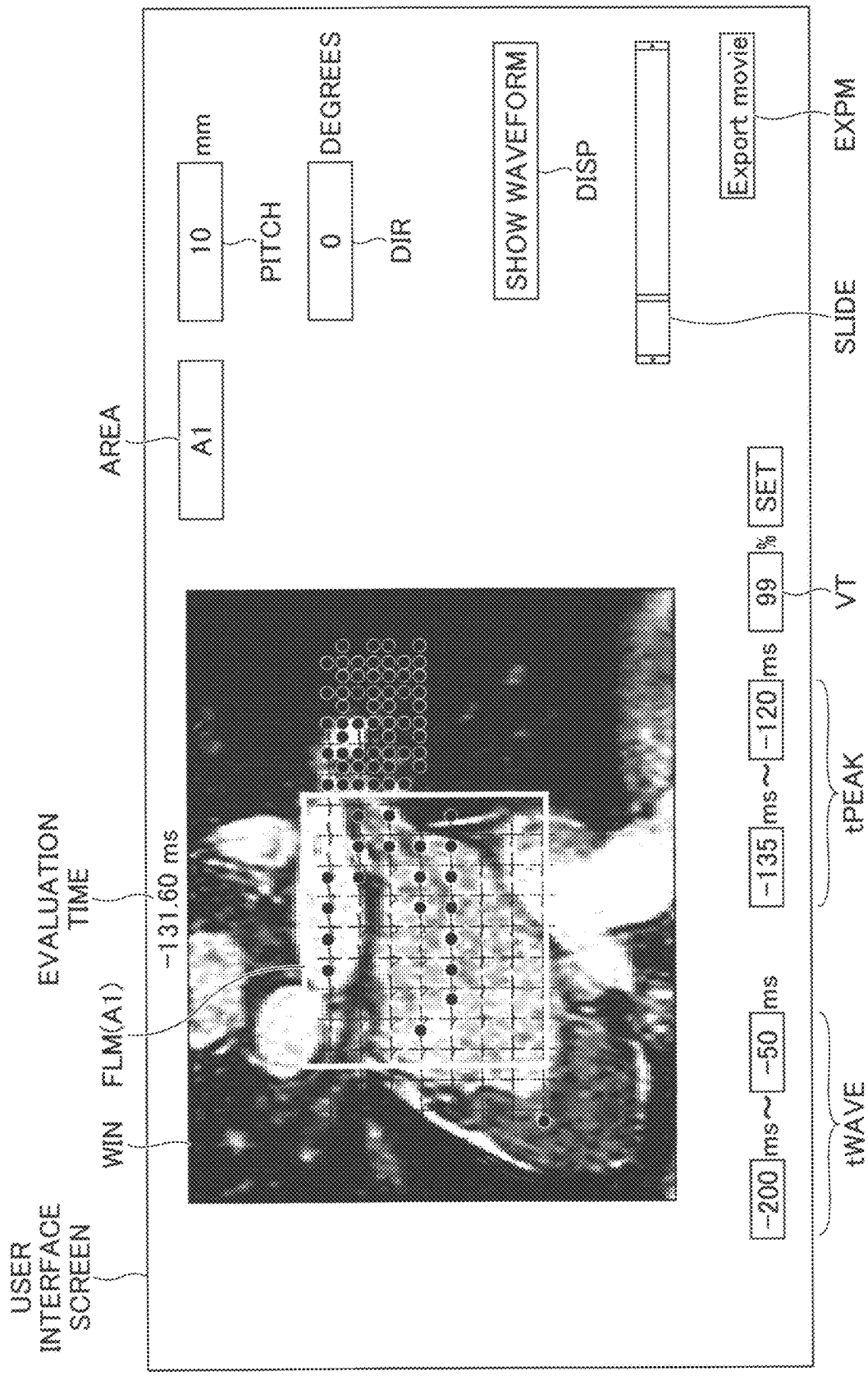
[Fig. 10]

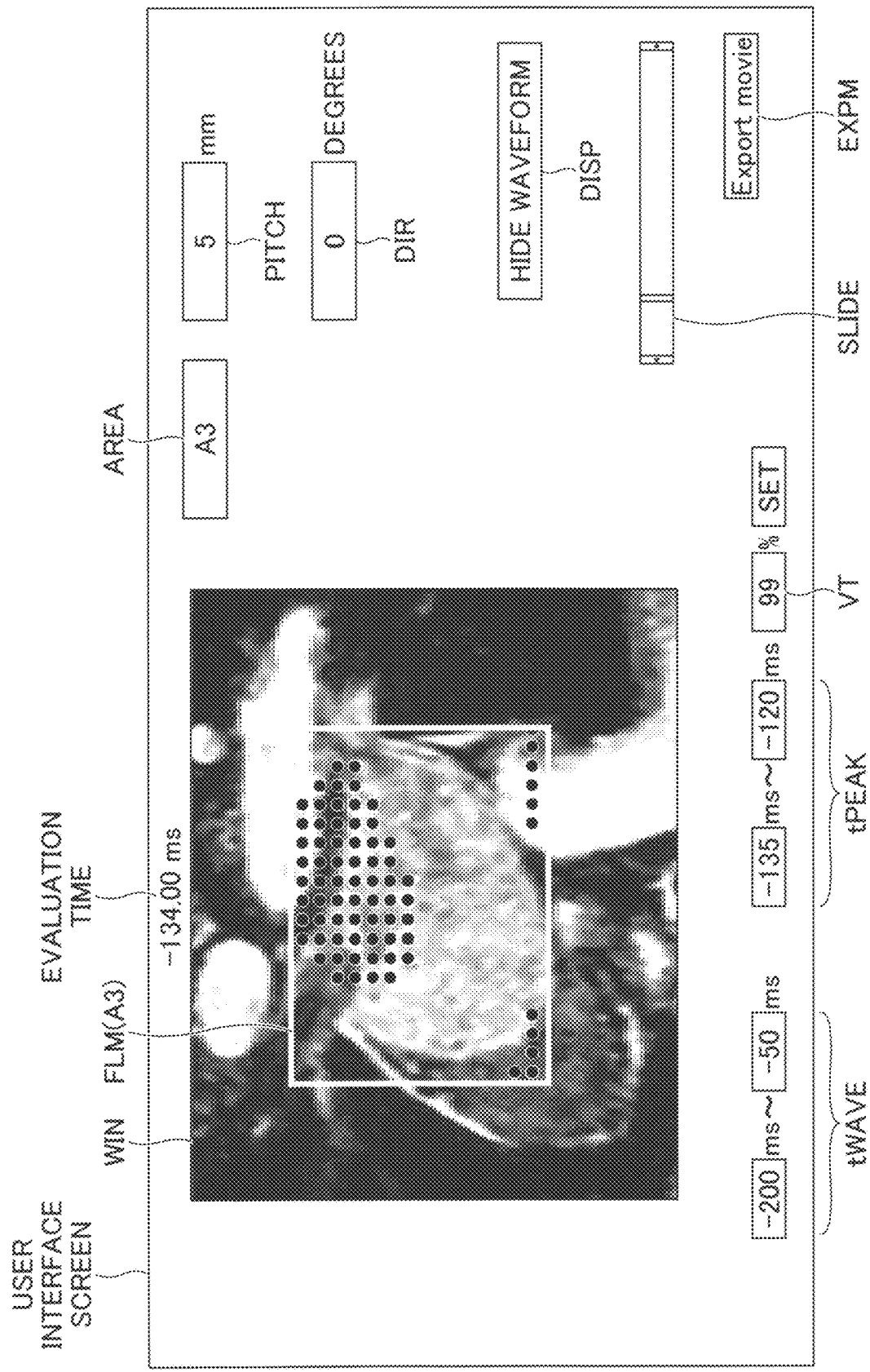
[Fig. 11]

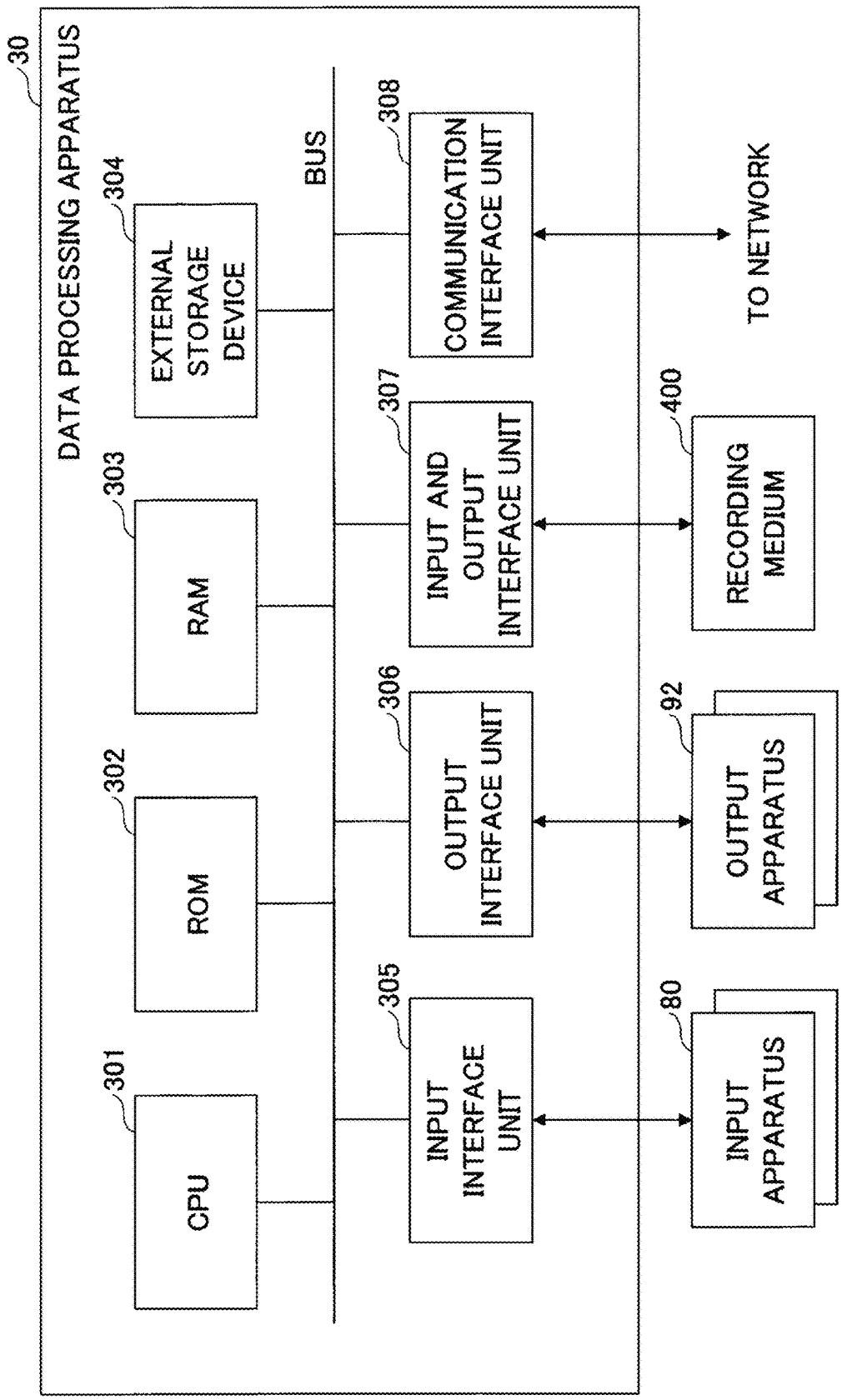
[Fig. 12]

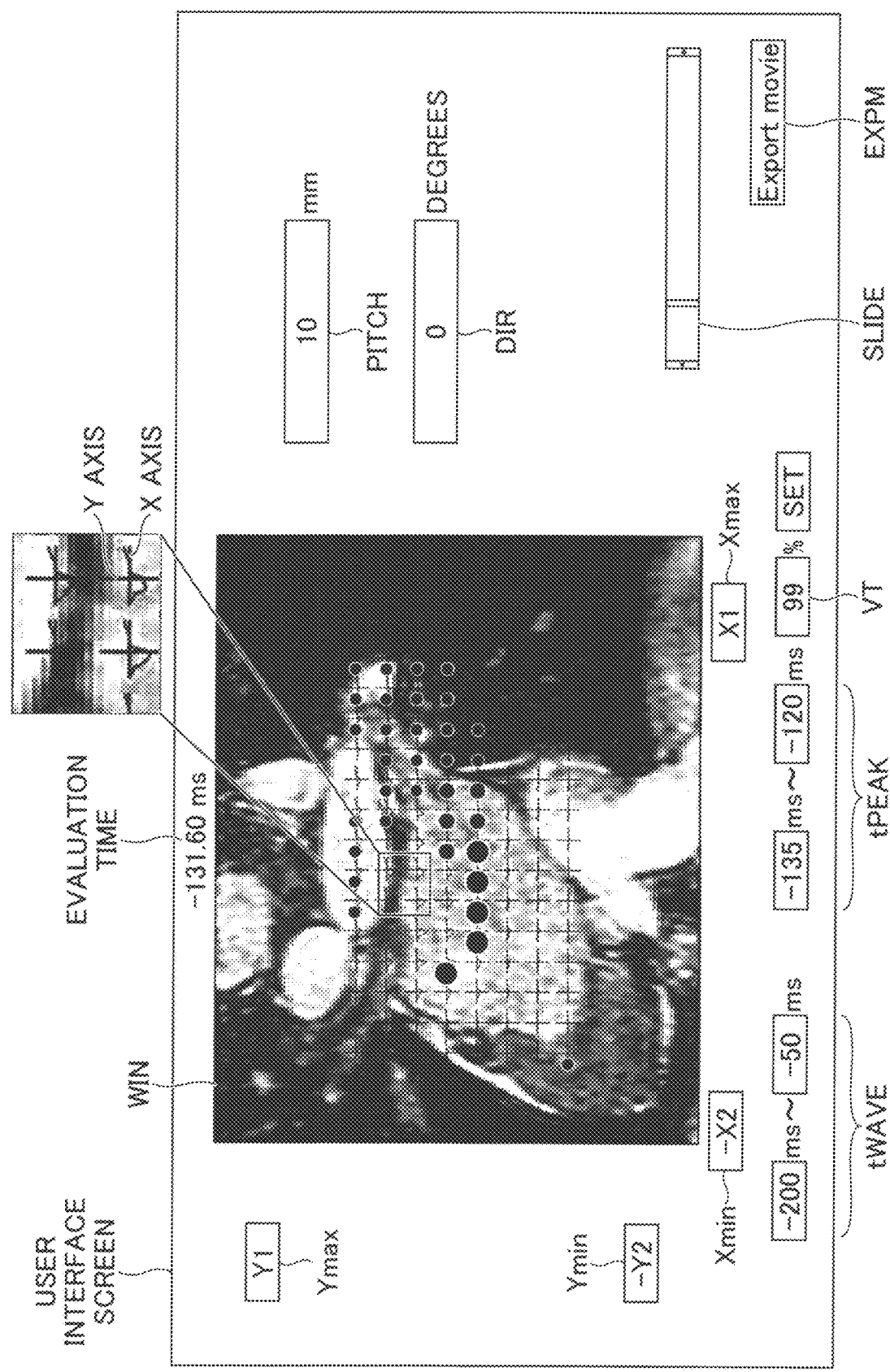
[Fig. 13]

BIOMETRIC INFORMATION DISPLAY APPARATUS, METHOD, AND PROGRAM

TECHNICAL FIELD

The present disclosure relates to a biometric information display apparatus, a biometric information display method, and a display program.

BACKGROUND ART

For example, with a biomagnetism measurement system configured to detect the magnetism generated from a living body with multiple magnetic sensors, PTL 1 suggests a method for dynamically displaying an isomagnetic field diagram, in which points of equal magnitudes of the magnetic field are connected, on a display apparatus by designating any given measurement time.

CITATION LIST

Patent Literature

[PTL 1] Japanese Unexamined Patent Application Publication No. H11-104093

SUMMARY OF INVENTION

Technical Problem

A biomagnetism measurement system can measure biomagnetism with a high sensitivity and a high spatial resolution. Therefore, the biomagnetism measurement system can measure, at a time, a relatively large magnetism and a relatively small magnetism which occur at multiple measurement portions close to each other. However, when the magnetisms that occur at multiple measurement portions or biometric signals such as currents calculated from the magnetisms are displayed on a display screen, the relatively small biometric signals are buried in the relatively large biometric signals, which results in a problem of the reduction in the visibility.

The present disclosure is made in view of the above problems, and it is an object of the present disclosure to improve the visibility when a measurement result of a relatively small biometric signal is displayed.

Solution to Problem

In order to solve the above problems, a biometric information display apparatus according to an aspect of the present invention is a biometric information display apparatus for displaying a measurement result obtained by measuring a biometric signal. The biometric information display apparatus includes a maximum value calculation unit configured to calculate a maximum value of the measurement result in a certain period of time for at least one of blocks into which a measurement area, in which the biometric signal is measured, is divided, a determination unit configured to determine whether a measurement value in the at least one of blocks is greater than or equal to a threshold value obtained by multiplying the maximum value by a fractional value, the fractional value being determined in advance, and a display control unit configured to display, in response to an occurrence of an event in which the measurement value is determined to be greater than or equal to the threshold value, the measurement result in such a manner as to indicate the occurrence of the event.

Advantageous Effects of Invention

The visibility can be improved when a measurement result of a relatively small biometric signal is displayed.

BRIEF DESCRIPTION OF DRAWINGS

FIG. 1 is a block diagram illustrating an example of a biometric information measurement apparatus including a biometric information display apparatus according to a first embodiment of the present invention.

FIG. 2 is an explanatory diagram illustrating an example of a user interface screen displayed on the display apparatus of FIG. 1.

FIG. 3 is a flowchart illustrating an example of operation of a data processing apparatus of FIG. 1.

FIG. 4 is a flowchart illustrating an example of step S50 of FIG. 3.

FIG. 5 is an explanatory diagram illustrating an example of changes in images displayed on the display apparatus of FIG. 1.

FIG. 6 is an explanatory diagram illustrating an example (Comparative Example) of changes in images displayed on a display apparatus of another biometric information measurement apparatus.

FIG. 7 is an explanatory diagram illustrating an example of changes in images in another measurement portion displayed on the display apparatus of FIG. 1.

FIG. 8 is an explanatory diagram illustrating an example (Comparative Example) of changes in images in another measurement portion displayed on a display apparatus of another biometric information measurement apparatus.

FIG. 9 is an explanatory diagram illustrating an example of a display screen displayed on a display apparatus of a biometric information measurement apparatus including a biometric information display apparatus according to a second embodiment of the present invention.

FIG. 10 is an explanatory diagram illustrating another example of a display screen displayed on the display apparatus of the biometric information measurement apparatus including the biometric information display apparatus according to the second embodiment of the present invention.

FIG. 11 is an explanatory diagram illustrating still another example of a display screen displayed on the display apparatus of the biometric information measurement apparatus including the biometric information display apparatus according to the second embodiment of the present invention.

FIG. 12 is a block diagram illustrating an example of hardware configuration of a data processing apparatus of FIG. 1.

FIG. 13 is an explanatory diagram illustrating another example of a user interface screen displayed on the display apparatus of FIG. 1.

DESCRIPTION OF EMBODIMENTS

Hereinafter, embodiments will be described with reference to the drawings. In each drawing, the same constituent elements may be denoted by the same reference numerals and duplicate explanations thereabout may be omitted.

First Embodiment

FIG. 1 is a block diagram illustrating an example of a biometric information measurement apparatus including a biometric information display apparatus according to the first embodiment of the present invention. For example, a biometric information measurement apparatus 100 illustrated in FIG. 1 includes a Superconducting QUantum Interference Device (SQUID) unit 10, a signal acquisition unit 20, a data processing apparatus 30, an input apparatus 80, and a display apparatus 90. The data processing apparatus 30 is a computer such as a Personal Computer (PC), a server, and the like, and functions as a biometric information display apparatus.

The signal acquisition unit 20 includes a Flux Locked Loop (FLL) circuit 21, an analog signal processing unit 22, an Analog-to-Digital (AD) conversion unit 23, and a Field-Programmable Gate Array (FPGA) 24. For example, the SQUID unit 10 and the signal acquisition unit 20 are installed in a shield room shielding the magnetism; and the data processing apparatus 30, the input apparatus 80, and the display apparatus 90 are installed outside of the shield room.

The data processing apparatus 30 includes an input control unit 40, a display control unit 50, an operation control unit 60, and a storage unit 70. The operation control unit 60 includes a measurement control unit 61, a current reconstruction unit 62, a current waveform generation unit 63, and an emphasis display determination unit 64. For example, the functions of the input control unit 40, the display control unit 50, and the operation control unit 60 are implemented by causing a processor such as a Central Processing Unit (CPU) provided in the data processing apparatus 30 to execute a display program to carry out the biological information display method in cooperation with hardware.

The biometric information measurement apparatus 100 includes a magnetoencephalograph (MEG), a magnetocardiograph (MCG), a magnetospinograph (MSG), or the like. The biometric information measurement apparatus 100 may be used to measure magnetic fields of the spinal cord but also magnetic fields of nerves or magnetic fields of muscles (i.e., magnetic fields generated in the skeletal muscles, myocardium, smooth muscles, and the like).

The SQUID unit 10 measures the magnetic field generated by a subject on the basis of an instruction from the measurement control unit 61, and outputs the measured magnetic field as voltage signals. For example, the SQUID unit 10 includes multiple SQUID sensors arranged to face the measurement portion of the magnetic field of the subject who lies on the bed. The FLL circuit 21 improves the dynamic range by linearizing the non-linear magnetic field-voltage characteristics measured by the multiple SQUID sensors.

For example, the SQUID sensor is a three-axis sensor with the X axis, the Y axis, and the Z axis, capable of measuring a magnetic field signal as a three-dimensional vector quantity. Alternatively, the SQUID sensor may be a two-axis sensor with the X axis and the Y axis, capable of measuring a magnetic field signal as a two-dimensional vector quantity, or may be a one-axis sensor with only the Z axis. In a case where the one-axis SQUID sensor with only the Z axis is used, a component in the X axis and a component in the Y axis (i.e., a two-dimensional vector quantity) are calculated from the measured biomagnetism signal. The three-axis SQUID sensor has a higher directional resolution than the one-axis SQUID sensor and the two-axis SQUID sensor, so that the three-axis SQUID sensor can improve the measurement accuracy of any given component in the X-Y direction to achieve more detailed evaluation.

The analog signal processing unit 22 amplifies a magnetic field signal (i.e., a voltage signal), which is a linearized analog signal output from the FLL circuit 21, and performs filter processing and the like on the amplified voltage signal. The AD conversion unit 23 converts the filtered magnetic field signal (i.e., the voltage signal) into a digital value to generate magnetic field data. The FPGA 24 further performs filter processing, interleave processing, and the like on the magnetic field data digitalized by the AD conversion unit 23, and transfers the processed magnetic field data to the data processing apparatus 30. Note that at least a part of the processing performed by the FPGA 24 may be performed by the data processing apparatus 30. The digitalized magnetic field data is an example of a biometric signal acquired from a subject (a living body).

The biometric information measurement apparatus 100 may include other magnetic sensors instead of the SQUID unit 10. The biometric information measurement apparatus 100 may include a potential measurement unit for measuring the potential of the evaluation target area of the subject instead of the SQUID unit 10 and the signal acquisition unit 20. For example, the potential measurement unit continuously measures the potential via multiple electrodes attached to the evaluation target area. For example, a current signal can be calculated as a two-dimensional vector quantity by causing the data processing apparatus 30 to process temporal changes in the measured potential signal.

In the data processing apparatus 30, the input control unit 40 receives various kinds of information from an operator, who operates the data processing apparatus 30, through an input apparatus 80 such as a mouse, a keyboard, and the like. Hereinafter, the operator of the data processing apparatus 30 may also be simply referred to as an operator. The operator may be an evaluator such as a doctor explained later. The display control unit 50 performs control to display, on a display apparatus 90 such as a liquid crystal display, an X-ray image, an MR image, current waveforms superimposed on the X-ray image or the MR image, and the like. In addition, the display control unit 50 performs control to display an image display window for displaying images and a user interface screen with which various kinds of conditions are input and displayed when current data are reconstructed from data of the measured magnetic field. The input apparatus 80 and the display apparatus 90 may be included in the data processing apparatus 30. In addition, an output apparatus such as a printer may be connected to the data processing apparatus 30.

In the operation control unit 60, the measurement control unit 61 controls the operation of the SQUID unit 10 and the signal acquisition unit 20. For example, when the biometric information measurement apparatus 100 functions as a magnetocardiograph, the measurement control unit 61 causes the SQUID unit 10 and the signal acquisition unit 20 to measure the magnetic field in accordance with a measurement start instruction received from the input apparatus 80 through the input control unit 40.

When the biometric information measurement apparatus 100 functions as a magnetoencephalograph, a magnetospinograph, or a myomagnetometer, the measurement control unit 61 causes the SQUID unit 10 and the signal acquisition unit 20 to measure the magnetic field in accordance with a synchronized signal from a stimulation apparatus giving an electrical stimulation and the like to the subject. The measurement control unit 61 performs control to receive biomagnetism data generated by the signal acquisition unit 20 on the basis of the magnetic field measured by the SQUID unit 10 and stores the received biomagnetism data in the storage unit 70. The stimulation given to the subject by the stimulation apparatus is not limited to an electrical stimulation, and the stimulation apparatus may give stimulation by magnetism, sound, or light, or may apply physical stimulation such as vibration and the like.

The current reconstruction unit 62 reconstructs current components (the orientation, strength, and the like) from the biomagnetism data stored in the storage unit 70, and stores the reconstructed current components in the storage unit 70. For example, the current components reconstructed from the biomagnetism data are three-dimensional vector data. For example, whereas the SQUID sensors are arranged with a distance of several centimeters between each other, the voxels which are calculation points of currents are arranged with a distance of several millimeters (for example, equal distances) between each other. Because the voxels which are calculation points of currents do not physically exist, the voxels are virtually arranged in programs reconstructing currents from the magnetic field data or in data used by such programs. In this case, the current reconstruction unit 62 reconstructs the current component in the direction indicated by the calculation direction of the current received from the input apparatus 80 with the input control unit 40. The calculation direction of the current is explained later with reference to FIG. 2. When the voxels are arranged with equal distances between each other, the current can be calculated from the magnetic field data by a simpler calculation method than in the case where the voxels are not arranged with equal intervals between each other.

The reconstruction of the current component by the current reconstruction unit 62 may be performed by using a linear interpolation method, or may be performed using a method with a Unit Gain REcursive Null Steering (UGRENS) filter studied by the inventors of the present application. The method using the UGRENS filter can perform calculation more accurately in a shorter period of time than the linear interpolation method. Note that the method of reconstructing currents from the magnetic field is not limited to the spatial filter method.

The current waveform generation unit 63 acquires current data that changes over the elapse of time for each voxel as a current waveform (i.e., a measurement result) on the basis of the current components calculated by the current reconstruction unit 62 and stored in the storage unit 70. The current waveform generation unit 63 causes the acquired current waveform to be displayed on the display apparatus 90 with the display control unit 50, and calculates the latency, which is the time when the current value attains the maximum level, on the basis of the acquired current waveform. In addition, the current waveform generation unit 63 calculates a maximum value of current data in a certain period of time for each voxel. The current waveform generation unit 63 is an example of a maximum value calculation unit.

The emphasis display determination unit 64 determines whether to display a current waveform with emphasis for each voxel at every measurement time, on the basis of a fractional value VT (explained later with reference to FIG. 2) received from the input apparatus 80 with the input control unit 40. When the emphasis display determination unit 64 determines to display a current waveform with emphasis on the basis of the determination result, the emphasis display determination unit 64 causes the current waveform to be displayed with emphasis on the display apparatus 90 with the display control unit 50. The current waveform may be displayed with emphasis by changing the display color of the current waveform, by displaying a figure (emphasis mark) with the current waveform, or by displaying only a figure. Such displaying with emphasis is explained later with reference to FIG. 2.

The storage unit 70 is implemented with a storage device such as, e.g., a hard disk drive (HDD), and includes areas for storing biomagnetism data 71, morphological data 72, and various kinds of setting values 73. The biomagnetism data 71 includes magnetic field data measured by the SQUID unit 10 and processed by the signal acquisition unit 20. The morphological data 72 includes X-ray image data captured by an X-ray image-capturing apparatus, not illustrated, or a magnetic resonance (MR) image data captured by a magnetic resonance imaging apparatus, and the like.

The morphological data 72 may include current waveform data generated for each voxel, emphasis mark data, and the like. The current waveform data and the emphasis mark data may be stored, as superimposing data which are displayed in a superimposed manner on a morphological image, in a separate area in the storage unit 70. Hereinafter, an X-ray morphological image of a subject generated from the X-ray image data is referred to as an X-ray image, and a cross-sectional image of a subject generated from MR image data is referred to as an MR image.

The setting values 73 are used to store various kinds of information displayed in a user interface screen on the display apparatus 90. Examples of the setting values 73 are explained later with reference to FIG. 2. Parameters and the like of filters (e.g., a high pass filter and a low pass filter) provided in the signal acquisition unit 20 may be stored as the setting values 73 in the storage unit 70.

FIG. 2 is an explanatory diagram illustrating an example of a user interface screen displayed on the display apparatus 90 of FIG. 1. For example, currents are reconstructed from the magnetic field data acquired by measuring the magnetic field generated by myocardial motions, and as illustrated in FIG. 2, the waveforms of the reconstructed currents and the emphasis marks are displayed for respective voxels in a superimposed manner on the morphological image.

Hereinafter, in an image display window WIN displayed on the user interface screen, a point corresponding to a voxel is referred to as a voxel point. The display control unit 50 operating on the basis of an instruction given by the operation control unit 60 controls the display apparatus 90 to display the user interface screen as illustrated in FIG. 2 on the display screen of the display apparatus 90. In the example as illustrated in FIG. 2, a morphological image (MR image) of the heart of which the magnetic field is measured by the magnetocardiograph is displayed in the image display window WIN.

The user interface screen includes the image display window WIN in which a morphological image and the like can be displayed, area coordinate input fields Ymax, Ymin, Xmax, and Xmin, waveform display time input fields tWAVE, peak detection time input fields tPEAK, and a fractional value input field VT. The user interface screen includes a pitch input field PITCH and a current calculation direction input field DIR. Hereinafter, the setting values 73, which are set using the respective input fields Ymax, Ymin, Xmax, Xmin, tWAVE, tPEAK, VT, PITCH, and DIR, will be hereinafter explained with reference to the names of the respective input fields.

Also, the user interface screen includes a slide bar SLIDE and a moving picture output button EXPM. When an operator slides the slide bar SLIDE, an evaluation time of current components displayed on the upper side of the image display window WIN is changed. When the operator presses the moving picture output button EXPM, an image displayed according to operation of the slide bar SLIDE is exported as moving picture data. The evaluation time is a relative time indicating a measurement time with respect to a reference time. The measurement time is a time at which the magnetic field signals used for calculating current components displayed on the morphological image in the image display window WIN were measured. For example, when the magnetic field generated by myocardial motions is measured, the reference time (0 ms) is a point in time when a heartbeat occurs. The evaluation time indicates the extent of time before the heart beat occurs. In this case, the evaluation time is of a negative value.

The entered area coordinates Ymax, Ymin, Xmax, and Xmin are used to set a rectangular area for calculating current waveforms in the image displayed in the image display window WIN. The rectangular area designated by the area coordinates Ymax, Ymin, Xmax, and Xmin is an example of area for calculating current waveforms. In the example as illustrated in FIG. 2, the designated area coordinates Ymax, Ymin, Xmax, and Xmin are "Y1", "−Y2", "X1", and "−X2". The current waveforms displayed in the image display window WIN are biometric signal waveforms derived from muscles obtained by restructuring current values from magnetic field signals that occur according to currents flowing due to myocardial motions.

The waveform display time input field tWAVE is used to set a time range for displaying the current waveforms. In the example as illustrated in FIG. 2, the time range for displaying the current waveforms is set to a range from "−200 ms" to "−50 ms". Where a point in time at which a heartbeat occurs (reference time) is defined as 0 ms, the time range is of negative values, because the time range indicates a length of time before the heartbeat.

The peak detection time input field tPEAK is used to set a time range used for detection of the latency (in this example, a time when a peak current appears). The time range set by the peak detection time input field tPEAK is included in the range of the waveform display time tWAVE. In the example as illustrated in FIG. 2, the peak detection time tPEAK is set to a range of "−135 ms" to "−120 ms". The peak detection time tPEAK is an example of a certain period of time. With the peak detection time tPEAK being set, a wrong latency is prevented from being detected due to noise waveforms and the like outside of the range of the peak detection time tPEAK.

The fractional value input field VT is used to set a fractional value VT for determining whether a current value is to be displayed with emphasis at each voxel point. For example, the maximum value (peak value) of the current, i.e., the measurement result, is defined as 100%, and the fractional value input field VT is represented as a percentage of any given current value with respect to 100% such that when the magnitude of the current value is greater than or equal to a threshold value obtained by multiplying the peak current value by the percentage entered in the fractional value input field VT, the current value is displayed with emphasis. In the example as illustrated in FIG. 2, when the current value at the evaluation time is greater than or equal to 99% of the peak current value, the current value is determined to be displayed with emphasis.

In this embodiment, the fractional value VT for determining whether to display any given current value with emphasis can be set with reference to the current value at the latency for each voxel point, so that, even in a measurement portion where an amount of current is relatively small, an evaluator such as a doctor can readily judge the latency from the image displayed in the user interface screen. With the fractional value VT being set, a current value is displayed with emphasis in a predetermined period of time around the latency, so that the visibility of the latency for an evaluator such as a doctor can be improved as compared with a case where the current value is displayed with emphasis only at the instance of the latency. In FIG. 2, the fractional value VT is set commonly for all the voxels, but the fractional value VT may be set individually for each of the voxels.

In addition, for each voxel, a current waveform and a figure for emphasis are displayed in a superimposed manner on the measurement target area of the morphological image, so that an evaluator such as a doctor who evaluates the function of the subject by seeing the user interface screen can readily recognize the association between the current flowing through the evaluation target area and the corresponding portion of the morphological image. In contrast, when the fractional value VT is represented as a current value, a voxel point of which the amount of current is less than amounts of currents in other voxel points is not displayed with emphasis, which makes it difficult for an evaluator such as a doctor to visually determine the latency.

The pitch input field PITCH is used to set a pitch of voxels in which currents are reconstructed. In the example as illustrated in FIG. 2, the pitch PITCH is set to "10 mm". In the range defined by the area coordinates Ymax, Ymin, Xmax, and Xmin, multiple blocks are set, with a pitch PITCH, in association with the respective voxels.

In the current calculation direction input field DIR, the operator sets, in angle, a target component direction, i.e., a direction in which currents (measurement values) are calculated. For example, in the user interface screen, the right-hand side direction is defined as "0 degrees", the lower side direction is defined as "90 degrees", the lefthand side direction is defined as "180 degrees", and the upper side direction is defined as "270 degrees". In the example as illustrated in FIG. 2, the current calculation direction DIR is set to "0 degrees (X direction)".

Current waveforms are calculated by setting the current calculation direction DIR according to the evaluation target area (a direction in which muscle fibers or neural fibers), so that clinically useful muscle-derived or nerve-derived current waveforms can be obtained. For example, the cardiac muscles do not extend in a single direction but extend in various directions, and accordingly, it is preferable to allow the operator to set the current calculation direction DIR to any desired direction.

In FIG. 2, the current calculation direction DIR is set commonly for all the voxels, but the current calculation direction DIR may be individually set for each of the voxels, or may be set for each of the voxel groups, each including a predetermined number of voxels. In this case, even in a case where muscles extend in various directions, the current calculation direction DIR may be set for each of the directions in which the muscles extend, so that clinically useful current waveforms can be obtained. In contrast, the potentials measured by what is termed as a catheter mapping using a catheter are scalar quantities. Therefore, with the catheter mapping, the current components calculated from the potentials cannot be divided into directions.

Note that the operation control unit 60 may set the current calculation direction DIR (i.e., the target component direction) on the basis of information received from the input control unit 40 with respect to operation performed by the operator on the input apparatus 80 with a mouse and the like. For example, an input mode for inputting the current calculation direction DIR may be prepared, and when the operator draws a straight line on the image display window WIN with the mouse, the operation control unit 60 may set the direction (angle) of the straight line drawn from a start point to an end point as the current calculation direction DIR.

In this embodiment, the current calculation direction DIR may be set to any given direction (greater than or equal to 0 degrees, and less than 360) in a plane including the X direction (i.e., the horizontal direction in FIG. 2) and the Y direction (i.e., the vertical direction in FIG. 2). Further, the current calculation direction DIR may be allowed to be set to any spherical direction which is a combination of not only the X and Y directions but also the Z direction. Also, the current calculation direction DIR may be set for each of the voxels, or may be set for each of the voxel groups, each including a predetermined number of voxels.

The operation control unit 60 controls the display control unit 50 to display the entered setting values Ymax, Ymin, Xmax, Xmin, tWAVE, tPEAK, VT, PITCH, and DIR on the user interface screen, and stores them as the setting values 73 in the storage unit 70. The storage unit 70 may store the default values of the setting values Ymax, Ymin, Xmax, Xmin, tWAVE, tPEAK, VT, PITCH, and DIR, in advance. The current reconstruction unit 62, the current waveform generation unit 63, and the emphasis display determination unit 64 perform processing by using the default values of setting values 73 not having been input from among the setting values Ymax, Ymin, Xmax, Xmin, tWAVE, tPEAK, VT, PITCH, and DIR.

In FIG. 2, current waveforms (temporal changes of current intensities) and indications for emphasis (black circles) at the evaluation time "−131.60 ms", displayed on the upper side of the image display window WIN, are displayed in a superimposed manner on the morphological image in the image display window WIN. In other words, in the image display window WIN, the current waveforms of which the current values at the evaluation time are located on the Y axis are displayed. At each voxel point, when the current value on the Y axis at the evaluation time "−131.60 ms" is 99% or more with respect to the peak current value at the latency, a black circle is displayed as an emphasis.

The black circle is an example of a figure indicating that the measurement value has been determined to be greater than or equal to a threshold value obtained by multiplying the maximum value (i.e., the peak current value) by a predetermined fractional value defined in advance. A block (voxel area) in which a black circle is displayed is an example of a positively-determined block in which the measurement value has been determined to be greater than or equal to the threshold value obtained by multiplying the maximum value (i.e., the peak current value) by a predetermined fractional value defined in advance and in which the determination result has been reflected. A block (voxel area) in which a black circle is not displayed is an example of a negatively-determined block in which the measurement value has been determined to be less than the threshold value obtained by multiplying the maximum value (i.e., the peak current value) by the predetermined fractional value defined in advance. The shape of the figures displayed in the blocks corresponding to the voxels is not limited to the black circles, and the color of the figures is not limited to black. Instead of displaying the black circles, the thicknesses of the current forms may be increased for emphasis.

In the enlarged view of the voxel area illustrated on the upper side of FIG. 2, each voxel point is located at the intersection between the X axis representing the time and the Y axis representing the current intensity (amplitude). As described above, the current value of the current waveform intersecting the Y axis is the current value at the evaluation time "−131.60 ms" displayed in the user interface screen. The scales (defined by the maximum values and the minimum values in the X axis and the Y axis) of the current waveforms displayed in the image display window WIN are the same for all of the voxel points.

When the image including the current waveforms and the like displayed in the image display window WIN is changed by operating the slide bar SLIDE, the current waveforms are moved in the X axis direction so that the current values at the evaluation time that is set by operating the slide bar SLIDE intersect the Y axis. At each voxel point, when the current value intersecting the Y axis in the current waveform is greater than or equal to the threshold value obtained by multiplying the maximum value (i.e., the peak current value) at the latency by the fractional value VT, a black circle is displayed, and when the current value is less than the fractional value VT, a black circle is not displayed.

When images and the like are displayed in color in the image display window WIN, the current waveforms in the voxels corresponding to the black circles may be displayed in red and the like for emphasis, instead of being emphasized with the black circles. Also, a circular mark of which the size is changed in accordance with the magnitude of the peak current at the latency may be displayed. Specifically, FIG. 13 illustrates an example in which, where the magnitude of the maximum value of the peak currents in all of the blocks is denoted as A, a large circular mark is displayed in a block with a current value of A×0.9 or more, a medium circular mark is displayed in a block with a current value of A×0.7 or more and less than A×0.9, and a small circular mark is displayed in a block with a current value of less than A×0.7. It is to be understood that how greatly the size of the circular mark is changed may be in any manner, and the circular mark may not be necessarily changed to three levels in size. For example, the circular mark may be changed to two levels in size, or may be changed to four levels or more in size. Also, a circular mark may be displayed in a color corresponding to the magnitude of the peak current at the latency. In a case where the circular marks are displayed in corresponding colors, a legend including a color bar (like an intensity bar indicating the intensity as illustrated in FIG. 6) indicating a correspondence between the magnitude of the current and the color may be displayed besides the image display window WIN. The shapes and the colors in the method for displaying the current values in the image display window WIN are not particularly limited as long as a voxel in which the current value is greater than or equal to the threshold value obtained by multiplying the maximum value (i.e., the peak current value) by the fractional value VT and a voxel in which the current value is less than the threshold value can be readily distinguished from each other.

FIG. 3 is a flowchart illustrating an example of operation of the data processing apparatus 30 as illustrated in FIG. 1. First, in step S10, the measurement control unit 61 measures the biomagnetism of the subject by controlling the SQUID unit 10 and the signal acquisition unit 20. For example, when the measurement control unit 61 measures the magnetic fields of nerves such as the brain and the spinal cord or measures the magnetic field of muscles, the measurement control unit 61 causes the SQUID unit 10 to measure the biomagnetism of the subject while an electrical stimulation is given to the peripheral nerves of the subject. The electrical stimulation is given to the subject by the stimulation apparatus connected to the signal acquisition unit 20 as illustrated in FIG. 1.

The measurement control unit 61 may measure the biomagnetism in advance before the flow as illustrated in FIG.

3 is performed. In this case, the data processing apparatus 30 does not perform step S10, and instead, the data processing apparatus 30 performs processing in step S20 and subsequent steps by using the biomagnetism data stored in the storage unit 70.

In step S20, the current reconstruction unit 62 reconstructs the current components on the basis of the magnetic field data of all the measurement points. The current reconstruction unit 62 stores current information including the intensities and coordinates of the currents acquired from reconstruction as the morphological data 72 in the storage unit 70. Note that when the storage unit 70 does not store setting values 73 such as VT, PITCH, DIR, and the like used in the processing in step S20 and subsequent steps, the default values are used.

Next, in step S30, current waveforms in the designated current calculation direction DIR are generated for each voxel. By using the current information stored in the storage unit 70, the current waveform generation unit 63 generates the current waveforms that change according to an elapse of the measurement time. Then, the operation control unit 60 controls the display control unit 50 to display current waveforms, corresponding to the evaluation time that is set with the slide bar SLIDE, in a superimposed manner on the morphological image such as an X-ray image, an MR image, and the like in the image display window WIN. The image on which the current waveforms are superimposed is not particularly limited as long as the evaluation target area of the subject can be seen in the image.

Next, in step S40, when current waveforms in respective voxels are desired to be displayed with emphasis according to current values at the evaluation time that has been set, the emphasis display determination unit 64 displays black circles and the like for emphasis in the image displayed in the image display window WIN.

Next, in step S50, the input control unit 40 receives inputs of various kinds of setting values 73 from the operator with the input apparatus 80, and stores the received setting values 73 in the storage unit 70. Hereinafter, the receiving of inputs of various kinds of setting value 73 is explained with reference to FIG. 4. For example, when it is difficult for the operator to see how the currents change from the current waveforms displayed with the emphasis in step S40, step S50 is performed to change the current calculation direction DIR and the fractional value VT on the basis of an operation performed by the operator.

Next, in step S60, when currents need to be reconstructed according to changed setting values 73, the operation control unit 60 proceeds to step S20, and when currents do not need to be reconstructed, the operation control unit 60 proceeds to step S70. For example, when a voxel in which a current has not been reconstructed occurs due to a change in area coordinates Ymax, Ymin, Xmax, and Xmin, the currents need to be reconstructed.

In step S70, when current waveforms need to be reconstructed according to changed setting values 73, the operation control unit 60 proceeds to step S30, and when current waveforms do not need to be reconstructed, the operation control unit 60 proceeds to step S40. For example, when at least one of the pitch PITCH and the current calculation direction DIR is changed, the currents need to be reconstructed. The processing in step S20 to step S70 is repeatedly performed until the biomagnetism is measured, until an operation is performed to close the user interface screen, or until the data processing apparatus 30 is turned off. When the slide bar SLIDE is operated, a current distribution (voxels displayed with emphasis) and the like corresponding to the evaluation time that is set by operating the slide bar SLIDE are displayed in the image display window WIN again.

FIG. 4 is a flowchart illustrating an example of step S50 of FIG. 3. The order of execution of processing in step S501 to step S512 such as the pair of steps S501 and S502, the pair of steps S503 and S504, and the like is not limited to the order illustrated in FIG. 4, and the setting of each pair may be performed successively.

When the input control unit 40 receives inputs of the area coordinates Ymax, Ymin, Xmax, and Xmin in step S501, the input control unit 40 stores the received area coordinates Ymax, Ymin, Xmax, and Xmin in the storage unit 70 in step S502 to set the received area coordinates Ymax, Ymin, Xmax, and Xmin as setting values 73.

When the input control unit 40 receives the pitch PITCH in step S503, the input control unit 40 stores the received pitch PITCH in the storage unit 70 in step S504 to set the received pitch PITCH as a setting value 73. When the input control unit 40 receives a waveform display time tWAVE in step S505, the input control unit 40 stores the received waveform display time tWAVE in the storage unit 70 in step S506 to set the received waveform display time tWAVE as a setting value 73.

When the input control unit 40 receives the peak detection time tPEAK in step S507, the input control unit 40 stores the received peak detection time tPEAK in the storage unit 70 in step S508 to set the received peak detection time tPEAK as a setting value 73. When the input control unit 40 receives the fractional value VT in step S509, the input control unit 40 stores the received fractional value VT in the storage unit 70 in step S510 to set the received fractional value VT as a setting value 73.

When the input control unit 40 receives the current calculation direction DIR in step S511, the input control unit 40 stores the received current calculation direction DIR in the storage unit 70 in step S512 to set the received current calculation direction DIR as a setting value 73. When the input control unit 40 determines that the inputs of all of the setting values 73 have been finished, the input control unit 40 terminates the processing in step S50. Whether the inputs have been finished may be determined on the basis of a termination instruction of reception entered by the operator with the input apparatus 80.

The setting values 73 stored in the storage unit 70 in the processing of step S50 as illustrated in FIG. 4 may be used when currents are reconstructed from other magnetic field data to display current waveforms and the like in the image display window WIN. In this case, in the processing of step S50, the determinations in steps S501, S503, S505, S507, S509, S511 are made as "NO", and thereafter, the determination in step S513 is made as "NO". Accordingly, the processing in step S50 can be substantially omitted, and the time it takes to set the setting values 73 can be reduced. In addition, when the same setting values 73 are used, the current data reconstructed from magnetic field data different from each other can be compared easily. A series of setting values 73 that are set in step S50 may be stored in the storage unit 70 with a group name, and the setting values 73 may be recalled and used by designating the group name.

FIG. 5 is an explanatory diagram illustrating an example of changes in images displayed on the display apparatus 90 of FIG. 1. Like FIG. 2, the image as illustrated in FIG. 5 includes a morphological image (MR image) of the heart of which the magnetic field is measured by magnetocardiograph. The method for displaying current waveforms and black circles for emphasis is the same as the method according to the flow as illustrated in FIG. 3. FIG. 5 illustrates only the image displayed in the image display window WIN of FIG. 2, but the configuration of the user interface screen for displaying the image is the same as the configuration of FIG. 2.

When the operator operates the slide bar SLIDE, the image displayed in the image display window WIN is changed in the order as indicated by the arrows in FIG. 5. A white solid circle in FIG. 5 indicates the position of the posterior wall of the left atrium, and is an area in which a relatively large magnetic field signal derived from the left atrium is measured. A white broken line circle illustrated in FIG. 5 indicates the position of a connection portion between the pulmonary vein and the heart, and is an area in which a relatively small magnetic field signal derived from the myocardium surrounding the pulmonary vein is measured. The white solid circles and the white broken line circles are attached for the sake of explanation, and are not actually displayed in the images.

When current information such as currents reconstructed from magnetic field data is displayed in a superimposed manner on a morphological image according to a conventional technique, the current information is displayed with a scale corresponding to a signal with a large current intensity. In this case, the current information about the myocardium connected to the pulmonary vein is difficult to recognize because it is buried in the current information about large currents derived from the left atrium, and it is difficult to evaluate the myocardium connected to the pulmonary vein.

For example, it has been reported that, in the heart, the myocardium signal connected to the pulmonary vein is the cause of atrial fibrillation. In this embodiment, black circles are not displayed with reference to the magnitudes of the currents, but are displayed with reference to the peak values of the currents in the respective voxels. Therefore, when the amplitudes of the currents are small, black circles can be displayed around an occurrence of a peak current, and conduction of a small current in the myocardium and the like can be visually recognized.

The fractional value VT is set for each voxel point, and therefore, even if a large magnetic field signal derived from the left atrium and a small magnetic field signal derived from the myocardium of the pulmonary vein are present at the same time, the current information about the myocardium of the pulmonary vein can be displayed with emphasis on the basis of a reference that is different from the current information about large currents derived from the left atrium.

Accordingly, as indicated by the white broken line circle, currents flowing in the right pulmonary vein at "−132.4 ms" and currents flowing in the left pulmonary vein at "−120.4 ms" can be displayed without being hidden by large currents derived from the left atrium. In other words, as compared with conventional methods, signals transmitted to the pulmonary vein can be displayed in a visually easy-to-understand manner.

For example, it is assumed that there are a first voxel of which the peak value of the current is "10" and a second voxel of which the peak value of the current is "100", and it is assumed that the fractional value VT is set to 90%. In this case, a black circle is displayed in the first voxel if the current value is greater than or equal to "9", and a black circle is displayed in the second voxel if the current value is greater than or equal to "90". Therefore, just like a large current, even a small current of which the peak value is about one-tenth can be emphasized with a black circle and the like in the image at the evaluation time at around the peak current.

When the operator operates the slide bar SLIDE with the input apparatus 80 such as a mouse, the operation control unit 60 reads a morphological image and the like from the storage unit 70 on the basis of an operation content received with the input control unit 40, and causes the display control unit 50 to display the morphological image.

Comparative Example

FIG. 6 is an explanatory diagram illustrating an example (Comparative Example) of changes in images displayed on a display apparatus of another biometric information measurement apparatus. In the image as illustrated in FIG. 6, (the directions and the intensities) of the current components reconstructed in respective voxels from the measured magnetic field are displayed in a superimposed manner on the morphological image (MR image) of the heart of which the magnetic field is measured by magnetocardiograph. The morphological image in FIG. 6 is similar to the morphological image as illustrated in FIG. 5. In the example as illustrated in FIG. 6, the current values at all the voxel points are displayed as arrows with lengths corresponding to the current intensities with the same scale. Curved lines in a manner of contour lines are current intensity distribution lines that indicate the positions of equal current intensities, and although it is difficult to see, a line of a lighter color indicates a higher current, and a line of a darker color indicates a lower current. When images and the like are displayed in color in the image display window WIN, the current intensity distribution lines may be displayed in different colors corresponding to the current intensities.

Just like FIG. 5, a white solid circle in FIG. 6 indicates the position of the posterior wall of the left atrium, and a white broken line circle illustrated in FIG. 6 indicates the position of a connection portion between the pulmonary vein and the heart. The white solid circles and the white broken line circles are attached for the sake of explanation. In order to evaluate the currents derived from the myocardium surrounding the pulmonary vein, it is important to be able to easily recognize the currents flowing in the connection portion between the pulmonary vein and the heart. However, as illustrated in FIG. 6, when information about the current intensity is displayed, the currents derived from the left atrium are relatively large and noticeable, whereas the currents derived from the myocardium surrounding the pulmonary vein are difficult to recognize and are difficult to evaluate.

FIG. 7 is an explanatory diagram illustrating an example of changes in images in another measurement portion displayed on the display apparatus 90 as illustrated in FIG. 1. In the example as illustrated in FIG. 7, the biometric information measurement apparatus 100 is caused to function as a magnetospinograph to measure the biomagnetism in the cervical spinal cord (nerves) of the subject in response to an electrical stimulation given by a stimulation apparatus, and a change in a current reconstructed from the magnetic field data is displayed for each voxel in a superimposed manner on an X-ray image of the subject. The current waveforms displayed in the image display window WIN are biometric signal waveforms derived from the nerves obtained by reconstructing current values from the magnetic field signals occurring according to the currents flowing due to the actions of the nerves. An evaluation time (for example, 7.0 ms) displayed on the upper side of the image display window WIN is a measurement time at which the magnetic field signals used for calculating the current components are measured, and indicates a length of time elapsed from a point in time (reference time=0 ms) of an electrical stimulation.

The method for displaying current waveforms and displaying black circles for emphasis is the same as the method according to the flow as illustrated in FIG. 3. FIG. 7 illustrates only the image displayed in the image display window WIN of FIG. 2, but the configuration of the user interface screen for displaying the image is the same as the configuration of FIG. 2. A white broken line circle as illustrated in FIG. 7 indicates a position beside the direction in which the nerves of the cervical spinal cord extend, which is the evaluation target area, and indicates a position to evaluate the current component (inward currents of depolarized portions) perpendicular to the direction in which the nerves of the cervical spinal cord extend. In the nerves, it is important to evaluate inward currents of depolarized portions. The white broken line circles are attached for the sake of explanation, and are not actually displayed in the images.

In FIG. 7, the current components (inward currents of depolarized portions) perpendicular to the direction in which the nerves of the cervical spinal cord extend, which are the valuation target area, are evaluated, and accordingly, the current calculation direction DIR is set to "0" degrees (the X direction, i.e., the horizontal direction of FIG. 5). Therefore, only the inward current components of depolarized portions can be displayed as black circles, and an evaluator such as a doctor can easily visually recognize conductions of inward currents of depolarized portions.

Comparative Example

FIG. 8 is an explanatory diagram illustrating an example (Comparative Example) of changes in images in another measurement portion displayed on a display apparatus of another biometric information measurement apparatus. In the image as illustrated in FIG. 8, (the directions and the intensities) of the current components reconstructed in respective voxels from the measured magnetic field are displayed in a superimposed manner on the morphological image (X-ray image) of the cervical spinal cord (nerves) of which the magnetic field is measured by magnetocardiograph. The morphological image in FIG. 8 is similar to the MORPHOLOGICAL image as illustrated in FIG. 7. Like FIG. 6, in the example as illustrated in FIG. 8, the current values at all the voxel points are displayed as arrows with lengths corresponding to the current intensities with the same scale. Like FIG. 6, curved lines in a manner of contour lines are current intensity distribution lines that indicate the positions of equal current intensities.

When currents are displayed as arrows with lengths corresponding to the current intensities, not only currents in the white broken line circle, which is the evaluation target area, but also current components (intraaxonal currents) flowing, outside of the white broken line circle, in parallel with the direction in which the nerves of the cervical spinal cord extend, and current components (volume currents) flowing around the axons are displayed prominently. Therefore, with only the directions and the magnitudes of the arrows, it is difficult to evaluate current components (inward currents of depolarized portions) perpendicular to the direction in which the nerves of the cervical spinal cord extend.

Hereinabove, in the first embodiment, for each voxel, a current value is determined as to whether a peak value of a current waveform is greater than or equal to the threshold value obtained by multiplying the maximum value (i.e., the peak current value) by the fractional value VT, and a black circle and the like indicating that the current value is close to the peak value is displayed for emphasis with a block corresponding to a voxel in which the peak value is greater than or equal to the threshold value obtained by multiplying the maximum value (i.e., the peak current value) by the fractional value VT. In this case, according to the fractional value VT, a black circle and the like indicating a positively-determined block is displayed for emphasis with a positively-determined block that is determined to be around the peak current, and the black circle is not displayed with a negatively-determined block other than the positively-determined block. Therefore, a measurement result of a relatively small biometric signal can be displayed in the image display window WIN, without being buried in a measurement result of a relatively large biometric signal. As a result, the visibility of the measurement result of the relatively small biometric signal in the image display window WIN can be improved, and even when the biometric signal of the evaluation target is relatively small, an evaluator such as a doctor can easily evaluate the conductions of the biometric signals while seeing the user interface screen.

For each voxel, the current waveform and the figure for emphasis are displayed in an overlapping manner on the morphological image of the measurement target area, and therefore, an evaluator such as a doctor can easily recognize the relative positions between the currents in the evaluation target area and the corresponding portions in the morphological image.

In the first embodiment, a magnetic field signal, which is a vector quantity, or a current signal, which is a vector quantity, are used. Therefore, the current calculation direction DIR for calculating the current waveforms can be set according to the evaluation target area (the direction in which muscle fibers or nerves extend). Because the current calculation direction DIR is set according to the direction in which muscle fibers or nerves extend, clinically useful muscle-derived or nerve-derived current waveforms can be obtained. For example, although current components of desired X-Y direction components can be obtained with a high precision by using a three-axis SQUID sensor of a high directional resolution, components in the X axis and components in the Y axis can be obtained from magnetic field data measured with a one-axis (the Z axis) SQUID sensor.

Second Embodiment

FIG. 9 is an explanatory diagram illustrating an example of a display screen displayed on a display apparatus of a biometric information measurement apparatus according to the second embodiment of the present invention. Constituent elements similar to FIG. 2 are denoted with the same reference numerals, and detailed explanation thereabout is omitted.

The user interface screen as illustrated in FIG. 9 is displayed on the display apparatus 90 of the biometric information measurement apparatus 100 as illustrated in FIG. 1. The morphological image, the current waveform, and the like displayed in the image display window WIN of the user interface screen are generated by the data processing apparatus 30 as illustrated in FIG. 1. Therefore, the biometric information measurement apparatus 100 as illustrated in FIG. 1 is different from the second embodiment in some of the functions of the input control unit 40 and the functions of the operation control unit 60. A morphological image (MR image) of the heart of which the magnetic field is measured by the magnetocardiograph is displayed in the image display window WIN of FIG. 9 in a manner similar to FIG. 2.

In this embodiment, multiple areas AREA can be set in the image display window WIN, and the pitch PITCH of voxels and the current calculation direction DIR can be set for each of the areas AREA. According to the pitch PITCH that has been set for each of the areas AREA, the voxels are arranged with equal distances.

In addition, a waveform display button DISP for switching ON or OFF the display of the current waveform for each voxel is added. In FIG. 9, "waveform display ON" is selected, and accordingly, black circles and current waveforms are displayed in the image display window WIN. The waveform display time tWAVE, the peak detection time tPEAK, and the fractional value VT are commonly set for all of the areas AREA. The fractional value VT may be set for each of multiple areas AREA, or may be set for each of the voxels.

For example, the area AREA is set by inputting an area name ("A2" in FIG. 9) to the area coordinate input field AREA and designating an area AREA (A2) in the image display window WIN. The area AREA may be designated by inputting a rectangular frame with the input apparatus 80 such as a mouse, or may be designated by inputting a closed curve of any shape (e.g., a polygon). Alternatively, the area AREA may be designated using the area coordinate input fields Ymax, Ymin, Xmax, and Xmin illustrated in FIG. 2. As long as the area AREA is in such a range that current values can be reconstructed from measurement data of the magnetic field, the range of the area AREA may be set outside of an area of an image displayed in the image display window WIN.

For example, the areas AREA that have been set in the past may be selected from a pull-down list that is displayed when the area coordinate input field AREA is clicked, and the selected area AREA may be displayed with emphasis by a white frame FLM (A2) in the image display window WIN. The pitch input field PITCH and the current calculation direction input field DIR are used to input the current calculation direction DIR (component direction) with respect to the selected area AREA (=A2).

When multiple areas AREA that have been set overlap with each other in the image display window WIN, an area AREA that is set later becomes valid in the overlapping portion. In the example as illustrated in FIG. 9, after the area AREA (=A1; Ymax=Y1, Ymin=−Y2, Xmax=X1, Xmin=−X2) similar to FIG. 2 is set, an area AREA (=A2) indicated by a white frame FLM (A2) is set to overlap with the area AREA (A1). The pitch PITCH of the area AREA indicated by the white frame FLM (A2) is set to "5 mm", and the current calculation direction DIR is set to "0 degrees". As explained with reference to FIG. 2, the current calculation direction DIR may be allowed to be set with the Z direction, and/or may be allowed to be set for each of the voxels or for each of the voxel groups.

In this embodiment, a predetermined number of areas AREA each being of any given size and being at any given position can be set, and the pitch PITCH of voxels and the current calculation direction DIR can be set for each of the areas AREA. Accordingly, for each evaluation target area of the subject, an emphasis (a black circle and the like) can be displayed according to the pitch PITCH and the current calculation direction DIR of the evaluation target area. Therefore, even when the value of the current flowing through the evaluation target area is small, an evaluator such as a doctor can easily evaluate the conductions of the biometric signals while seeing the user interface screen.

FIG. 10 is an explanatory diagram illustrating another example of a display screen displayed on a display apparatus of a biometric information measurement apparatus including the biometric information display apparatus according to the second embodiment of the present invention. Constituent elements similar to FIG. 9 are denoted with the same reference numerals, and detailed explanation thereabout is omitted. The example as illustrated in FIG. 10 illustrates a user interface screen in which the area AREA (=A1) is selected. For example, the pitch PITCH of the area AREA indicated by the white frame FLM (A1) is set to 10 mm, and the current calculation direction DIR is set to 0 degrees.

FIG. 11 is an explanatory diagram illustrating still another example of a display screen displayed on a display apparatus of a biometric information measurement apparatus including the biometric information display apparatus according to the second embodiment of the present invention. Constituent elements similar to FIG. 9 are denoted with the same reference numerals, and detailed explanation thereabout is omitted. The example as illustrated in FIG. 11 illustrates a user interface screen in which an area AREA (=A3) is selected. For example, the pitch PITCH of the area AREA indicated by the white frame FLM (A3) is set to 5 mm, and the current calculation direction DIR is set to 0 degrees. In FIG. 11, "waveform display OFF" is selected by the waveform display button DISP. As a result, the current waveforms corresponding to the voxels are not displayed in the white frame FLM (A3). For example, the details of the morphological image can be displayed in an easy-to-see manner by hiding the current waveforms, and an evaluator such as a doctor can easily recognize the relative positions between the currents in the evaluation target area and the corresponding portions in the morphological image.

Hereinabove, according to the second embodiment, effects similar to the first embodiment explained above can be obtained. For example, a measurement result of a relatively small biometric signal can be displayed in the image display window WIN, without being buried in a measurement result of a relatively large biometric signal. As a result, the visibility of the measurement result of the relatively small biometric signal in the image display window WIN can be improved, and even when the biometric signal of the evaluation target is relatively small, an evaluator such as a doctor can easily evaluate the conductions of the biometric signals while seeing the user interface screen.

Further, in the second embodiment, multiple areas AREA can be set, and the pitch PITCH of voxels and the current calculation direction DIR can be set independently in each of the multiple areas AREA. Accordingly, an emphasis (a black circle and the like) can be displayed according to the pitch PITCH for each evaluation target area of the subject. In this case, the magnetic field signal or the current signal, which is a vector quantity, is used, and therefore, according to the evaluation target area (a direction in which the muscle fibers or the nerves extend), the current calculation direction DIR can be set, and the current waveforms can be calculated. As a result, even when the value of the current flowing through the evaluation target area is small, an evaluator such as a doctor can obtain clinically useful muscle-derived or nerve-derived current waveforms, and can easily evaluate the conductions of the signals while seeing the user interface screen.

FIG. 12 is a block diagram illustrating an example of hardware configuration of a data processing apparatus 30 of FIG. 1. The data processing apparatus 30 includes a CPU 301, ROM (Read Only Memory) 302, RAM (Random Access Memory) 303, and an external storage device 304. Also, the data processing apparatus 30 includes an input interface unit 305, an output interface unit 306, an input and output interface unit 307, and a communication interface unit 308. For example, the CPU 301, the ROM 302, the RAM 303, the external storage device 304, the input interface unit 305, the output interface unit 306, the input and output interface unit 307, and the communication interface unit 308 are connected to each other by a bus BUS.

The CPU 301 executes various kinds of programs such as an OS and applications to control the entire operation of the data processing apparatus 30. The ROM 302 holds basic programs for executing various kinds of programs with the CPU 301, various kinds of parameters, and the like. The RAM 303 stores various kinds of programs executed by the CPU 301 and data used by the programs. The external storage device 304 is an HDD (Hard Disk Drive), an SSD (Solid State Drive), or the like, and stores the various kinds of programs which are extracted to the RAM 303. The various kinds of programs may include display programs for displaying current waveforms reconstructed from magnetic field data on the display apparatus 90.

The input interface unit 305 is connected to the input apparatus 80 such as a keyboard, a mouse, and a tablet that receives inputs from an operator or the like who operates the data processing apparatus 30. The output interface unit 306 is connected to an output apparatus 92 (for example, the display apparatus 90 of FIG. 1) such as a printer or a display apparatus for displaying a display screen and the like generated by various kinds of programs executed by the CPU 301.

The input and output interface unit 307 is connected to a recording medium 400 such as USB (Universal Serial Bus) memory and the like. For example, the recording medium 400 stores various kinds of programs such as the display program and the like explained above for displaying current waveforms on the display apparatus 90. In this case, the programs are transferred via the input and output interface unit 307 from the recording medium 400 to the RAM 303. The recording medium 400 may be a CDROM, a Digital Versatile Disc (DVD, registered trademark), and the like. In this case, the input and output interface unit 307 includes an interface according to the connected recording medium 400. The communication interface unit 308 connects the data processing apparatus 30 to a network and the like.

In the embodiment explained above, the example for displaying, on a screen, waveforms of currents reconstructed from biomagnetism data of the subject has been explained. However, for example, a magnetic field signal estimated for each voxel by using the biomagnetism data of the subject may be displayed on a screen. In other words, signals displayed on the screen may be other than currents, as long as the signals can be represented as vector quantities. For example, for each voxel, a magnetic field signal that is determined to be greater than or equal to a threshold value obtained by multiplying the maximum value (i.e., the peak current value) by a fractional value defined in advance with respect to a maximum value of the magnetic field signal is displayed with emphasis. When the magnetic field signals are displayed, the measured magnetic field signals can be used as they are, and therefore, complicated signal processing for reconstructing current signals is not needed. When magnetic field signals that can be expressed as vector quantities are used in a manner similar to the current signals, only the components of the magnetic field signals in the direction that is set by the operator can be displayed in a superimposed manner on the morphological image. Further, waveforms and the like of the magnetic field signals can be displayed in a selective manner according to the chronological order. Therefore, on the basis of a change in the magnetic field signals, an evaluator can verify where the signal source (current source) is located and in which direction the signals are flowing.

Alternatively, the potentials of the evaluation target area of the subject may be measured at multiple locations, a current signal may be calculated from a difference between the measured potentials, and the calculated current signal may be displayed on the screen. In this case, for each voxel, a current signal that is determined to be greater than or equal to a fractional value defined in advance with respect to a maximum value of the current signal is displayed with emphasis. The currents occur according to the actions in the living body, and therefore, when current signals are displayed in a superimposed manner on the morphological image, an evaluator can easily visually ascertain an evaluation as to in which portion and to what degree the signals occur. In this manner, the magnetic fields and the currents are useful for physiological evaluation because the components can be decomposed into desired directions.

Although the present invention has been hereinabove explained on the basis of the embodiments, the present invention is not limited to the features of the above embodiments. These features can be changed without deviating from the gist of the present invention, and can be appropriately determined according to the form of application.

REFERENCE SIGNS LIST

10 SQUID unit
20 signal acquisition unit
21 FLL circuit
22 analog signal processing unit
23 AD conversion unit
24 FPGA
30 data processing apparatus
40 input control unit
50 display control unit
60 operation control unit
61 measurement control unit
62 current reconstruction unit
63 current waveform generation unit
64 emphasis display determination unit
70 storage unit
71 biomagnetism data
72 morphological data
73 setting value
80 input apparatus
90 display apparatus
100 biometric information measurement apparatus
301 CPU
302 ROM
303 RAM
304 external storage device
305 input interface unit
306 output interface unit
307 input and output interface unit
308 communication interface unit
400 recording medium
AREA area
DIR current calculation direction
DISP waveform display button
EXPM moving picture output button
FLM white frame PITCH interval
SLIDE slide bar
tPEAK peak detection time
tWAVE waveform display time
VT fractional value
WXmax, Xmin, Ymax, Ymin area The present application is based on and claims the benefit of priorities of Japanese Priority Application No. 2019-213566 filed on Nov. 26, 2019, and Japanese Priority Application No. 2020-074272 filed on Apr. 17, 2020, the contents of which are incorporated herein by reference.

The invention claimed is:

1. A biometric information display apparatus for displaying a measurement result obtained by measuring a biometric signal, comprising:
a maximum value calculation unit configured to calculate a maximum value of an electric current waveform in a certain time period for each of a plurality of blocks into which a measurement area is divided, the measurement area being an area in which the biometric signal is measured, the each of the plurality of blocks having the electric current waveform representing temporal changes of electric current values measured in the each of the plurality of blocks;
a determination unit configured to determine for the each of the plurality of blocks whether a value of the electric current waveform in the certain time period in the each of the plurality of blocks is greater than or equal to a threshold value, the threshold value being obtained by multiplying the maximum value calculated for the each of the plurality of blocks by a predetermined fractional value specific to the each of the plurality of blocks; and
a display control unit configured to display the electric current waveform for the each of the plurality of blocks in a manner indicating an occurrence of an event, in response to determining that the value of the electric current waveform in the certain time period in the each of the plurality of blocks is greater than or equal to the threshold value.

2. The biometric information display apparatus according to claim 1, wherein the plurality of blocks includes:
a positively-determined block in which the value of the electric current waveform within the certain time period is determined to be greater than or equal to the threshold value; and
a negatively-determined block in which the value of the electric current waveform within the certain time period is determined to be less than the threshold value,
wherein the positively-determined block is displayed in a manner different from the negatively-determined block.

3. The biometric information display apparatus according to claim 2, wherein a figure indicating that the value of the electric current waveform within the certain time period is determined to be greater than or equal to the threshold value is displayed with the positively-determined block.

4. The biometric information display apparatus according to claim 2, wherein the electric current waveform in the each of the plurality of blocks is displayed with the each of the plurality of blocks, and
the electric current waveform of the positively-determined block is displayed in a manner different from the electric current waveform of the negatively-determined block.

5. The biometric information display apparatus according to claim 1, wherein the display control unit displays a morphological image of a living body for the measurement area,
the display control unit sets the plurality of blocks on the displayed morphological image, and
the display control unit displays, for the each of the plurality of blocks, the electric current waveform superimposed on the displayed morphological image in such a manner as to indicate the occurrence of the event.

6. The biometric information display apparatus according to claim 5, wherein the display control unit sets the plurality of blocks in at least one of a plurality of areas in the displayed morphological image, and
the display control unit sets a size of the each of the plurality of blocks for the at least one of the plurality of areas.

7. The biometric information display apparatus according to claim 5, wherein the biometric signal is a magnetic field signal which is a vector quantity, a current signal which is a vector quantity calculated from a measured magnetic field, or a current signal which is a vector quantity calculated from a measured potential,
the display control unit sets the plurality of blocks in at least one of a plurality of areas in the displayed morphological image, and
the display control unit sets a component direction of the electric current waveform, which is a vector quantity, for the at least one of the plurality of areas.

8. The biometric information display apparatus according to claim 1, wherein the biometric signal is a magnetic field signal which is a vector quantity, a current signal which is a vector quantity calculated from a measured magnetic field, or a current signal which is a vector quantity calculated from a measured potential.

9. The biometric information display apparatus according to claim 8, wherein the display control unit sets a component direction of the electric current waveform, and
the maximum value is a maximum value of the electric current waveform in the component direction.

10. The biometric information display apparatus according to claim 9, wherein the electric current waveform in the component direction is obtained from the biometric signal measured by a sensor having one or more axes.

11. The biometric information display apparatus according to claim 1, wherein the biometric signal is a signal derived from a skeletal muscle, myocardium, smooth muscle, or nerve of a living body.

12. A biometric information display method executed by a biometric information display apparatus displaying a measurement result obtained by measuring a biometric signal, the biometric information display method comprising:
calculating a maximum value of an electric current waveform in a certain period of time for each of a plurality of blocks into which a measurement area is divided, the measurement area being an area in which the biometric signal is measured, the each of the plurality of blocks having the electric current waveform representing temporal changes of electric current values measured in the each of the plurality of blocks;
determining for the each of the plurality of blocks whether a value of the electric current waveform in the certain time period in the each of the plurality of blocks is greater than or equal to a threshold value, the threshold value being obtained by multiplying the maximum value calculated for the each of the plurality of blocks by a predetermined fractional value specific to the each of the plurality of blocks; and displaying the electric current waveform for the each of the plurality of blocks in a manner indicating an occurrence of an event, in response to determining that the value of the electric current waveform in the certain time period in the each of the plurality of blocks is greater than or equal to the threshold value.

13. A non-transitory computer-readable recording medium storing a display program executed by a biometric information display apparatus displaying a measurement result obtained by measuring a biometric signal, the display program causing the biometric information display apparatus to perform operations comprising:

calculating a maximum value of an electric current waveform in a certain period of time for each of a plurality of blocks at least one block from among blocks-into which a measurement area is divided, the measurement area being an area in which the biometric signal is measured, the each of the plurality of blocks having the electric current waveform representing temporal changes of electric current values measured in the each of the plurality of blocks;

determining for the each of the plurality of blocks whether a value of the electric current waveform in the certain time period in the each of the plurality of blocks is greater than or equal to a threshold value, the threshold value being obtained by multiplying the maximum value calculated for the each of the plurality of blocks by a predetermined fractional value specific to the each of the plurality of blocks; and displaying the electric current waveform for the each of the plurality of blocks in a manner indicating an occurrence of an event, in response to determining that the value of the electric current waveform in the certain time period in the each of the plurality of blocks is greater than or equal to the threshold value.

* * * * *